US012376750B2

(12) United States Patent
Madabhushi et al.

(10) Patent No.: US 12,376,750 B2
(45) Date of Patent: *Aug. 5, 2025

(54) TUMOR CHARACTERIZATION AND OUTCOME PREDICTION THROUGH QUANTITATIVE MEASUREMENTS OF TUMOR-ASSOCIATED VASCULATURE

(71) Applicants: Case Western Reserve University, Cleveland, OH (US); The United States Government as Represented by The Department of Veteran Affairs, Washington, DC (US)

(72) Inventors: Anant Madabhushi, Shaker Heights, OH (US); Nathaniel Braman, Bethel Park, PA (US)

(73) Assignees: Case Western Reserve University, Cleveland, OH (US); The United States Government as Represented by The Department of Veteran Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/495,821

(22) Filed: Oct. 27, 2023

(65) Prior Publication Data

US 2024/0057874 A1 Feb. 22, 2024

Related U.S. Application Data

(63) Continuation of application No. 17/116,319, filed on Dec. 9, 2020, now Pat. No. 11,896,349.

(Continued)

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0035* (2013.01); *A61B 5/004* (2013.01);
(Continued)

(58) Field of Classification Search
CPC ........... G06K 2209/051; G06K 9/0014; G06K 9/00147; G06K 9/46; G06K 9/4614;
(Continued)

(56) References Cited

U.S. PATENT DOCUMENTS

| 2014/0301619 | A1 | 10/2014 | Stavros et al. |
| 2017/0039737 | A1 | 2/2017 | Madabhushi et al. |
| 2017/0193657 | A1 | 7/2017 | Madabhushi et al. |

OTHER PUBLICATIONS

Braman, Nathaniel M., et al. "Intratumoral and peritumoral radiomics for the pretreatment prediction of pathological complete response to neoadjuvant chemotherapy based on breast DCE-MRI." Breast Cancer Research 19 (2017): 1-14.*

(Continued)

*Primary Examiner* — Carolyn A Pehlke
(74) *Attorney, Agent, or Firm* — Eschweiler & Potashnik, LLC

(57) ABSTRACT

The present disclosure relates to a method. The method may be performed by accessing data derived from one or more routine clinical medical imaging scans including a lesion in which the lesion and associated vasculature are segmented in a three-dimensional segmentation. At least two features are extracted from the three-dimensional segmentation of the associated vasculature. The at least two features include at least one feature indicative of a morphology of the associated vasculature or a portion thereof, and at least one feature indicative of a function of the associated vasculature or a portion thereof. The at least two features, and/or one or more statistics of the at least two features, are provided to a machine learning model trained to make a prediction con- (Continued)

cerning the lesion. The prediction concerning the lesion is received from the machine learning model.

20 Claims, 21 Drawing Sheets

Related U.S. Application Data

(60) Provisional application No. 62/945,310, filed on Dec. 9, 2019.

(51) Int. Cl.
  *A61B 5/08* (2006.01)
  *G06T 7/00* (2017.01)
  *G06T 7/12* (2017.01)

(52) U.S. Cl.
  CPC .............. *A61B 5/08* (2013.01); *A61B 5/7267* (2013.01); *A61B 5/7275* (2013.01); *G06T 7/0012* (2013.01); *G06T 7/12* (2017.01); *G06T 2207/10081* (2013.01); *G06T 2207/10088* (2013.01); *G06T 2207/20036* (2013.01); *G06T 2207/20081* (2013.01); *G06T 2207/30061* (2013.01); *G06T 2207/30068* (2013.01); *G06T 2207/30096* (2013.01); *G06T 2207/30101* (2013.01)

(58) Field of Classification Search
  CPC ........... A61B 6/032; A61B 6/463; A61B 6/50; A61B 6/12; G06T 2207/30096; G06T 2207/30061; G06T 2207/20152; G06T 2207/20081; G06T 2207/20076; G06T 2207/10081; G06T 7/0012; G06T 7/12; G06T 7/11; G06T 7/187; G06T 7/136
  See application file for complete search history.

(56) References Cited

OTHER PUBLICATIONS

Jason Brownlee (How to Choose a Feature Selection Method for Machine Learning, www.machinelearningmastery.com/feature-selection-with-real-and-categorical-data/, Nov. 27, 2019).
Non-Final Office Action dated Dec. 22, 2022 for U.S. Appl. No. 17/116,319.
Final Office Action dated May 17, 2023 for U.S. Appl. No. 17/116,319.
Notice of Allowance dated Sep. 27, 2023 for U.S. Appl. No. 17/116,319.

\* cited by examiner

| | Training set (n=98) | | Validation set (n=144) | | Combined (n=242) | |
|---|---|---|---|---|---|---|
| | Univariable | Multivariable | Univariable | Multivariable | Univariable | Multivariable |
| | OR / p | OR / p | OR / p | OR / p | OR / p | OR / p |
| QuanTAV Response Score | 0.09 (0.01-0.90) / 0.046 | 0.05 (0.00-0.87) / 0.040 | 0.07 (0.01-0.63) / 0.018 | 0.02 (0.00-0.32) / 0.005 | 0.08 (0.02-0.39) / 0.002 | 0.03 (0.00-0.23) / 0.001 |
| Hormone Receptor Status | 4.73 (1.77-12.65) / 0.002 | 5.99 (2.01-17.79) / 0.001 | 5.10 (2.02-12.90) / 0.001 | 7.24 (2.49-21.05) / <1E-5 | 4.92 (2.51-9.64) / <1E-5 | 6.31 (3.00-13.27) / <1E-5 |
| Age | 1.02 (0.97-1.07) / 0.495 | 1.06 (0.99-1.12) / 0.072 | 1.06 (1.01-1.11) / 0.012 | 1.06 (1.01-1.12) / 0.019 | 1.04 (1.01-1.07) / 0.020 | 1.05 (1.02-1.09) / 0.004 |
| Lesion Diameter | 1.17 (0.96-1.41) / 0.115 | 1.23 (0.98-1.53) / 0.069 | 1.09 (0.93-1.28) / 0.268 | 1.05 (0.88-1.26) / 0.559 | 1.12 (0.99-1.27) / 0.067 | 1.11 (0.97-1.28) / 0.114 |

| | Training set (n=98) | | Validation set (n=144) | | Combined (n=242) | |
|---|---|---|---|---|---|---|
| | UVA | MVA | UVA | MVA | UVA | MVA |
| QuanTAV response score | 0.030 | 0.030 | 0.015 | 0.0054 | 0.0012 | 0.00044 |
| Hormone Receptor Status | 0.0013 | 0.0013 | 0.00026 | 0.00028 | 1.00E-06 | 1.19E-06 |
| Age | 0.50 | 0.068 | 0.0098 | 0.019 | 0.0187 | 0.0039 |
| Lesion Diameter | 0.11 | 0.070 | 0.27 | 0.56 | 0.065 | 0.12 |

| | Training set (n=53) | | | | | Validation set (n=44) | | | | | Combined (n=97) | | | | |
|---|---|---|---|---|---|---|---|---|---|---|---|---|---|---|---|
| | Univariable | | Multivariable | | | Univariable | | Multivariable | | | Univariable | | Multivariable | | |
| | OR | p | OR | p | | OR | p | OR | p | | OR | p | OR | p | |
| QuanTAV Response Score | 0.04 (0.00–0.45) | 0.010 | 0.03 (0.00–0.47) | 0.013 | | 0.04 (0.00–0.62) | 0.021 | 0.03 (0.00–0.86) | 0.040 | | 0.04 (0.01–0.25) | 0.001 | 0.04 (0.01–0.27) | 0.001 | |
| Histology (Adenocarcinoma vs. SCC/other) | 0.24 (0.04–1.28) | 0.094 | 0.26 (0.03–2.38) | 0.231 | | 1.17 (0.35–3.89) | 0.802 | 1.92 (0.41–9.03) | 0.406 | | 0.65 (0.26–1.60) | 0.347 | 0.80 (0.28–2.29) | 0.683 | |
| Clinical stage | 1.02 (0.50–2.10) | 0.950 | 1.08 (0.39–3.03) | 0.881 | | 1.32 (0.75–2.33) | 0.335 | 1.18 (0.61–3.72) | 0.772 | | 1.19 (0.77–1.83) | 0.428 | 1.08 (0.58–2.01) | 0.813 | |
| History of smoking | 3.75 (0.68–20.63) | 0.129 | 6.49 (0.59–72.00) | 0.127 | | 0.67 (0.16–2.79) | 0.579 | 0.32 (0.05–2.24) | 0.253 | | 1.42 (0.51–3.97) | 0.505 | 1.33 (0.40–4.40) | 0.646 | |
| Sex | 0.37 (0.12–1.12) | 0.078 | 0.35 (0.09–1.39) | 0.134 | | 0.83 (0.25–2.72) | 0.763 | 0.86 (0.20–3.75) | 0.843 | | 0.54 (0.24–1.21) | 0.133 | 0.48 (0.19–1.23) | 0.125 | |
| Age | 0.94 (0.89–1.00) | 0.048 | 0.96 (0.89–1.03) | 0.243 | | 1.03 (0.98–1.07) | 0.232 | 1.04 (0.98–1.10) | 0.182 | | 1.00 (0.97–1.03) | 0.800 | 1.00 (0.96–1.04) | 0.940 | |

| | Training set (n=53) | | | Validation set (n=44) | | | Combined (n=97) | | |
|---|---|---|---|---|---|---|---|---|---|
| | Univariable | | Multivariable | Univariable | | Multivariable | Univariable | | Multivariable |
| | OR | p | OR p | OR | p | OR p | OR | p | OR p |
| QuanTAV Response Score | 0.04 | 0.010 | 0.03 0.013 | 0.04 | 0.011 | 0.03 0.040 | 0.04 | 0.001 | 0.04 0.001 |
| Histology (Adenocarcinoma vs. SCC/other) | 0.24 | 0.094 | 0.26 0.231 | 1.17 | 0.802 | 1.92 0.406 | 0.65 | 0.347 | 0.80 0.683 |
| Clinical stage | 1.02 | 0.950 | 1.08 0.881 | 1.32 | 0.335 | 1.18 0.772 | 1.19 | 0.428 | 1.08 0.813 |
| History of smoking | 3.75 | 0.129 | 6.49 0.127 | 0.67 | 0.579 | 0.32 0.253 | 1.42 | 0.505 | 1.33 0.646 |
| Sex | 0.37 | 0.078 | 0.35 0.134 | 0.83 | 0.763 | 0.86 0.843 | 0.54 | 0.133 | 0.48 0.125 |
| Age | 0.94 | 0.048 | 0.96 0.243 | 1.03 | 0.232 | 1.04 0.182 | 1.00 | 0.800 | 1.00 0.940 |

| | Training set (n=53) | | Validation set (n=44) | | Combined (n=97) | |
|---|---|---|---|---|---|---|
| | UVA | MVA | UVA | MVA | UVA | MVA |
| QuanTAV response score | 0.0054 | 0.013 | 0.014 | 0.040 | 0.00018 | 0.0010 |
| Histology (Adenocarcinoma vs. SCC/other) | 0.077 | 0.23 | 0.60 | 0.41 | 0.35 | 0.68 |
| Clinical stage | 0.46 | 0.88 | 0.57 | 0.77 | 0.60 | 0.81 |
| History of smoking | 0.11 | 0.13 | 0.58 | 0.25 | 0.50 | 0.65 |
| Sex | 0.075 | 0.13 | 0.76 | 0.84 | 0.13 | 0.13 |
| Age | 0.041 | 0.24 | 0.23 | 0.18 | 0.80 | 0.94 |

| | UVA | | MVA Risk Score (Continuous) | | MVA Risk Groups (Categorical) | |
|---|---|---|---|---|---|---|
| | Hazard Ratio (95% CI) | p-value | Hazard Ratio (95% CI) | p-value | Hazard Ratio (95% CI) | p-value |
| QuanTAV risk score (increase of .1) | 1.12 (0.96 - 1.31) | 0.141 | 1.07 (0.90 - 1.28) | 0.451 | -- | -- |
| TAV Risk Group (High vs. Low Risk) | 2.29 (1.07 - 4.94) | 0.034 | -- | -- | 2.20 (0.93 - 5.20) | 0.071 |
| Histology (adenocarcinoma vs. SCC/other | 0.79 (0.38 - 1.65) | 0.526 | 0.93 (0.43 - 2.03) | 0.863 | 0.92 (0.42 - 2.00) | 0.825 |
| Stage (per stage increase) | 1.16 (0.73 - 1.83) | 0.531 | 1.49 (0.73 - 3.05) | 0.279 | 1.73 (0.80 - 3.77) | 0.165 |
| Smoking history (Smoker vs. Non-smoker) | 0.67 (0.30 - 1.51) | 0.332 | 0.79 (0.32 - 1.92) | 0.598 | 0.83 (0.34 - 2.02) | 0.683 |
| Sex (male vs. female) | 1.10 (0.54 - 2.24) | 0.785 | 1.35 (0.58 - 3.17) | 0.485 | 1.47 (0.64 - 3.36) | 0.367 |
| Age (per year increase) | 0.99 (0.96 - 1.02) | 0.657 | 1.00 (0.97 - 1.03) | 0.826 | 1.00 (0.97 - 1.03) | 0.929 |
| RECIST response (Response/ stable disease vs. progression) | 0.58 (0.28 - 1.20) | 0.141 | 0.69 (0.31 - 1.53) | 0.359 | 0.81 (0.36 - 1.84) | 0.620 |

FIG. 14

| Variable | UVA Hazard Ratio (95% CI) | p | MVA Risk Score (Continuous) Hazard Ratio (95% CI) | p | MVA Risk Groups (Continuous) Hazard Ratio (95% CI) | p |
|---|---|---|---|---|---|---|
| QuantAV risk score (increase of 1) | 1.28 (1.01 - 1.62) | 0.039 | 2.92 (1.06 - 8.00) | 0.037 | - | - |
| TAV Risk Group (High vs Low Risk) | 3.77 (1.09 - 13.00) | 0.036 | - | - | 29.57 (2.07 - 422.11) | 0.013 |
| Histology (Adenocarcinoma vs. SCC/other) | 2.18 (0.79 - 6.02) | 0.13 | 6.66 (0.69 - 63.98) | 0.10 | 9.91 (0.79 - 124.48) | 0.076 |
| Presence of Vascular invasion | 3.56 (1.34 - 9.47) | 0.011 | 4.13 (0.66 - 25.69) | 0.13 | 12.28 (1.36 - 110.55) | 0.025 |
| Presence of lymphatic invasion | 2.42 (0.98 - 6.00) | 0.056 | 1.08 (0.15 - 7.71) | 0.94 | 1.85 (0.26 - 12.89) | 0.54 |
| Age (per year increase) | 1.03 (0.96 - 1.07) | 0.24 | 1.01 (0.93 - 1.10) | 0.82 | 1.05 (0.95 - 1.16) | 0.35 |
| Sex (male vs. female) | 1.16 (0.48 - 2.82) | 0.74 | 0.19 (0.02 - 2.13) | 0.18 | 0.46 (0.09 - 2.37) | 0.35 |
| Stage (per stage increase) | 1.17 (0.34 - 3.99) | 0.81 | 1.39 (0.20 - 9.60) | 0.74 | 0.70 (0.08 - 5.73) | 0.74 |
| Chemotherapy regimen (Carboplatin vs. Cisplatin) | 0.39 (0.11 - 1.34) | 0.13 | 0.25 (0.02 - 2.41) | 0.23 | 0.42 (0.05 - 3.32) | 0.41 |
| ECOG Performance Status (per grade increase) | 1.55 (0.35 - 6.77) | 0.56 | 10.44 (0.90 - 121.3) | 0.061 | 9.22 (1.09 - 77.69) | 0.041 |
| Induction Dose (per Gy increase) | 0.98 (0.93 - 1.04) | 0.54 | 1.04 (0.95 - 1.14) | 0.37 | 1.03 (0.93 - 1.13) | 0.59 |
| Major pathologic response (MPR) | 0.57 (0.23 - 1.42) | 0.23 | 0.41 (0.03 - 4.70) | 0.47 | 2.98 (0.16 - 54.74) | 0.46 |
| Response on pre-surgical imaging | 0.68 (0.26 - 1.77) | 0.43 | 4.74 (0.56 - 40.44) | 0.15 | 2.86 (0.30 - 27.16) | 0.36 |

FIG. 15

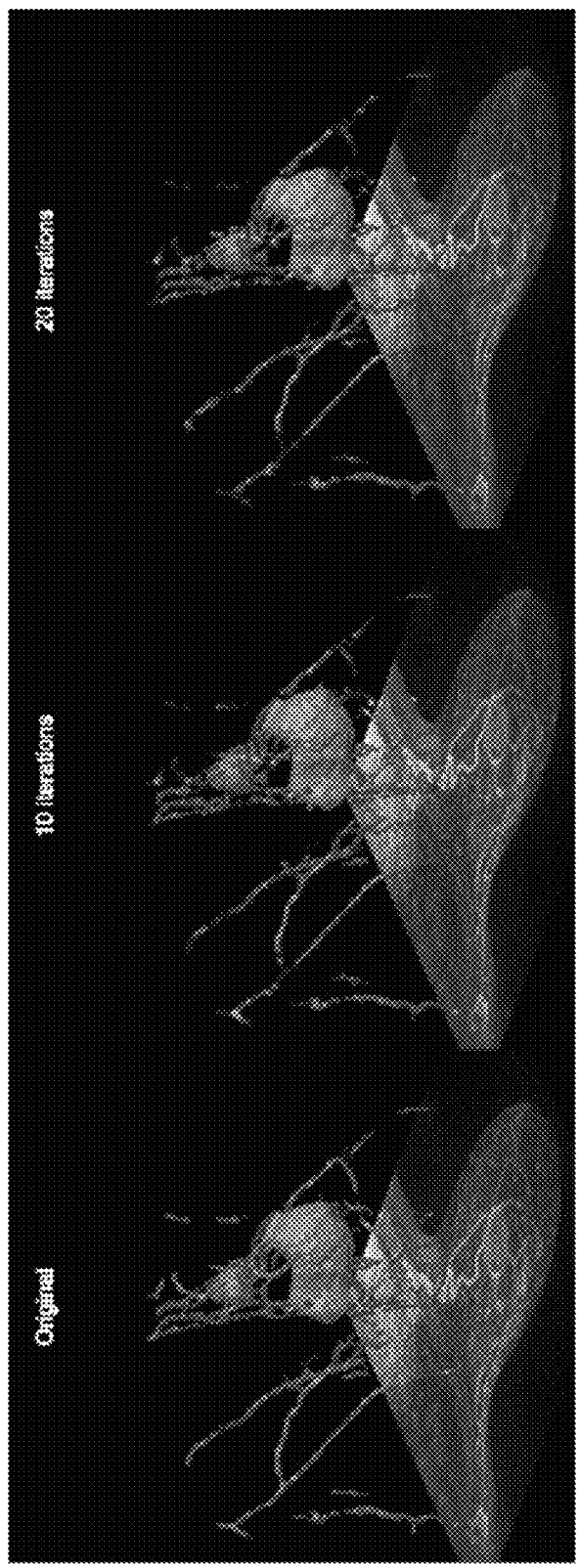 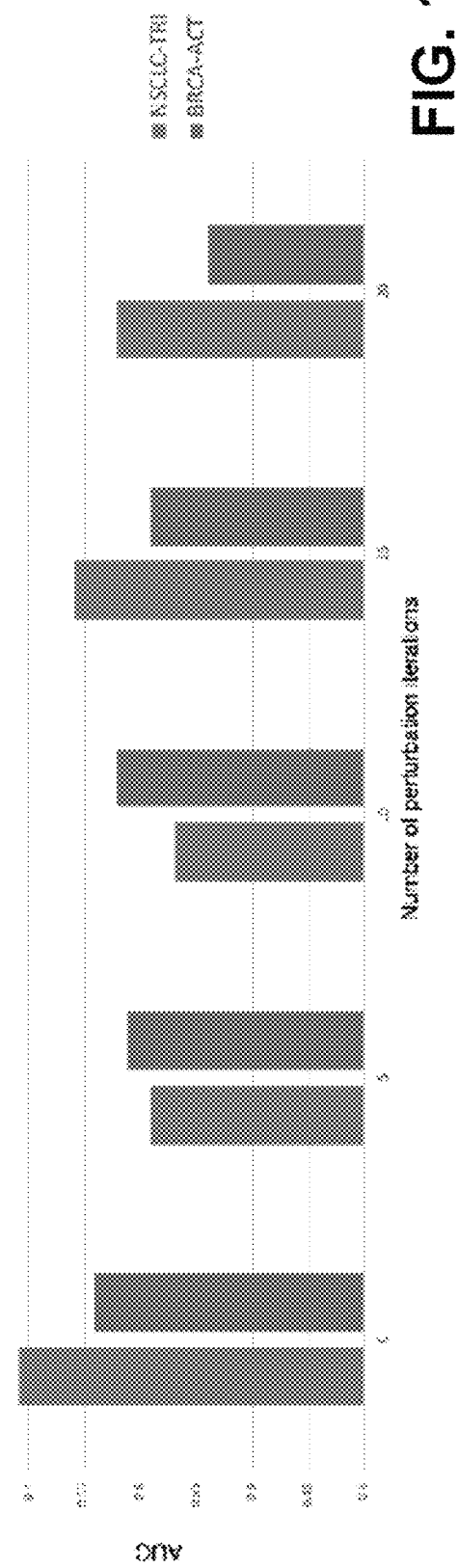
FIG. 16

FIG. 20

TUMOR CHARACTERIZATION AND OUTCOME PREDICTION THROUGH QUANTITATIVE MEASUREMENTS OF TUMOR-ASSOCIATED VASCULATURE

REFERENCE TO RELATED APPLICATIONS

This Application is a Continuation of U.S. application Ser. No. 17/116,319, filed on Dec. 9, 2020, which claims the benefit of U.S. Provisional Application No. 62/945,310, filed on Dec. 9, 2019. The contents of the above-referenced Patent Applications are hereby incorporated by reference in their entirety.

FEDERAL FUNDING NOTICE

This invention was made with government support under grant(s) CA199374, CA202752, CA208236, CA216579, CA220581, CA221383, EB007509, RR012463, and CA233216, awarded by the National Institutes of Health; and grant(s) IBX004121A awarded by the United States Department of Veterans Affairs; and grants W8IXWH-15-1-0558, W8IXWH-18-1-0440, and W8IXWH-16-1-0329 awarded by the Department of Defense. The government has certain rights in the invention.

BACKGROUND

Angiogenesis is crucial to a tumor's growth and an important factor in therapeutic outcome. Although quantitative analysis of tumors on dynamic contrast enhanced (DCE) magnetic resonance imaging (MRI) can provide indirect characterization of a tumor's vascularization, direct computational analysis of the tumor-associated vessel network remains an under-explored potential marker of therapeutic response. For instance, surrounding vasculature with a convoluted 3-dimensional (3D) shape and poor blood flow may indicate a more aggressive tumor, and poorly facilitate delivery of therapeutic agents.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 10 illustrates tables showing univariate (UVA) and multivariable (MVA) analysis of QuanTAV response score and available clinical variables for prediction of pCR to BRCA-ACT, in connection with various aspects discussed herein.

FIG. 11 illustrates tables showing univariate (UVA) and multivariable (MVA) analysis of QuanTAV response score and available clinical variables for prediction of pCR to BRCA-TCHP, in connection with various aspects discussed herein.

FIG. 13 illustrates tables showing univariate (UVA) and multivariable (MVA) analysis of QuanTAV response score and available clinical variables for prediction of RECIST response in NSCLC-PLAT recipients, in connection with various aspects discussed herein.

FIG. 14 illustrates a table showing Cox proportional hazard univariate (UVA) and multivariable (MVA) analysis of 10-year progression free survival following NSCLC-PLAT treatment, including QuanTAV risk score and available clinical variables, in connection with various aspects discussed herein.

FIG. 15 illustrates a table showing Cox proportional hazard univariate (UVA) and multivariable (MVA) analysis of 10-year recurrence free survival following NSCLC-TRI treatment, including QuanTAV risk score and available clinical variables, in connection with various aspects discussed herein.

FIG. 16 illustrates example images and a bar graph evaluating the robustness of QuanTAV-based response prediction to errors in vessel segmentation within a breast MRI (BRCA-ACT, n=141) and lung CT (NSCLC-TRI, n=46) testing set, in connection with various aspects discussed herein.

FIG. 20 illustrates tables showing univariate (UVA) and multivariable (MVA) analysis of QuanTAV response score and available clinical variables for prediction of major pathologic response (MPR) in NSCLC-TRI recipients, in connection with various aspects discussed herein.

DETAILED DESCRIPTION

Figure 1:
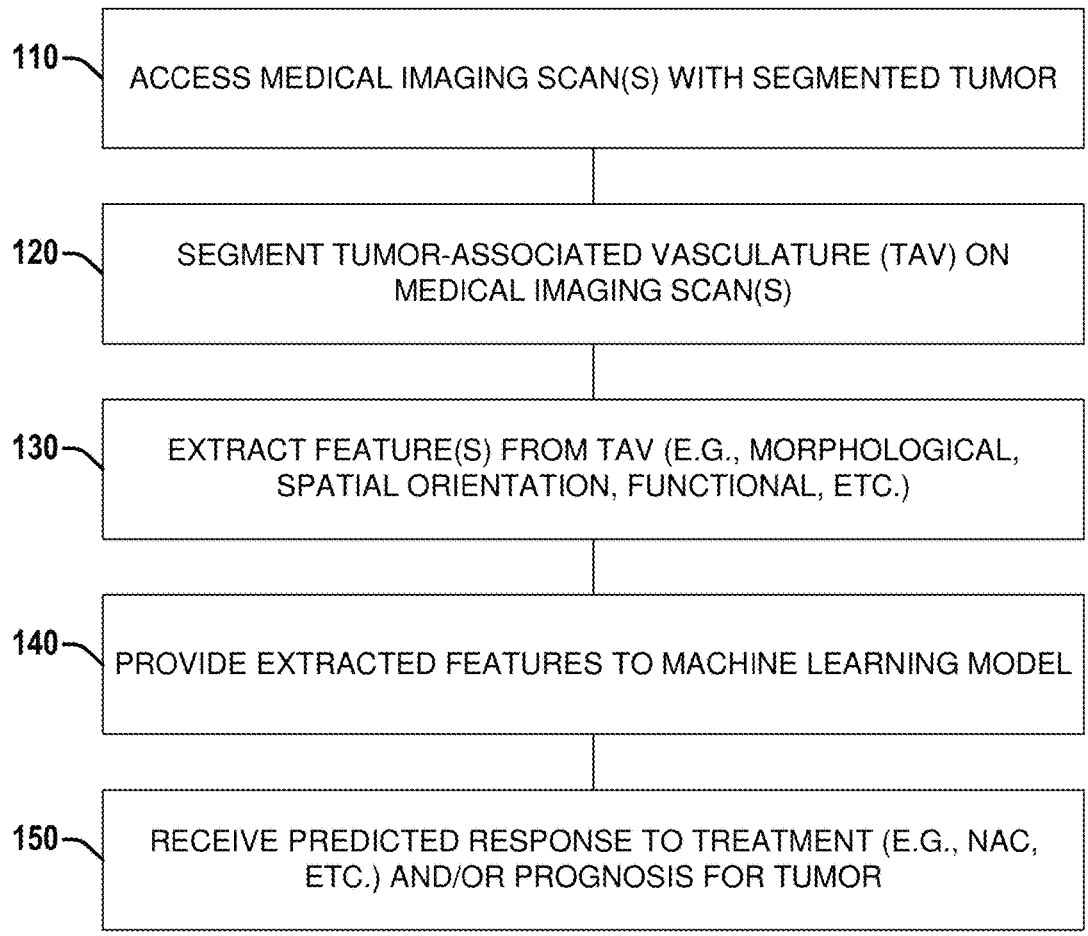
FIG. 1 illustrates a flow diagram of an example method/set of operations that can be performed by one or more processors to determine a therapy response and/or prognosis of a tumor based at least in part on morphological, spatial organization, and/or functional features of tumor-associated vasculature (TAV), according to various aspects discussed herein.

Various embodiments discussed herein can construct and/or employ models to determine a response to treatment and/or a prognosis for a tumor based at least in part on features of tumor-associated vasculature.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Embodiments include apparatus, systems, operations, methods, or other embodiments that can predict neoadjuvant therapy response and/or disease prognosis using a computational approach based on quantitative imaging features describing the morphology, spatial organization, and function of tumor associated vasculature. Embodiments can identify, extract, and/or analyze properties of the tumor-associated vessel network, such as its shape and enhancement profile, and generate a prediction of response, to facilitate identifying patients who will respond to neoadjuvant therapy before administration of treatment and/or to determine a prognosis for the tumor.

Referring to FIG. 1, illustrated is a flow diagram of an example method/set of operations 100 that can be performed by one or more processors to determine a therapy response and/or prognosis of a tumor based at least in part on morphological, spatial organization, and/or functional features of tumor-associated vasculature (TAV), according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing medical imaging (e.g., MRI, CT) scan(s) of a tumor (e.g., segmented on the scan, or as discussed herein) comprising a plurality of voxels. In various embodiments and in the example use cases discussed below, the imaging scan(s) can be obtained via a system and/or apparatus implementing the set of operations 100, or can be obtained from a separate medical imaging system. Additionally, the imaging scan(s) can be accessed contemporaneously with or at any point prior to performing the set of operations 100.

The set of operations 100 can further comprise, at 120, segmenting tumor-associated vasculature (TAV) associated with the tumor based on the medical imaging scan(s).

The set of operations 100 can further comprise, at 130, extracting one or more features from the TAV (e.g., morphological features, spatial organization features, functional features, etc.).

The set of operations 100 can further comprise, at 140, providing the one or more features extracted from the TAV to a trained machine learning model.

The set of operations 100 can further comprise, at 150, receiving, from the machine learning model, one of a predicted response to a treatment for the tumor or a prognosis for the tumor.

Additionally, or alternatively, set of operations 100 can comprise one or more other actions discussed herein in connection with determining a treatment response and/or prognosis of a tumor.

Figure 2:
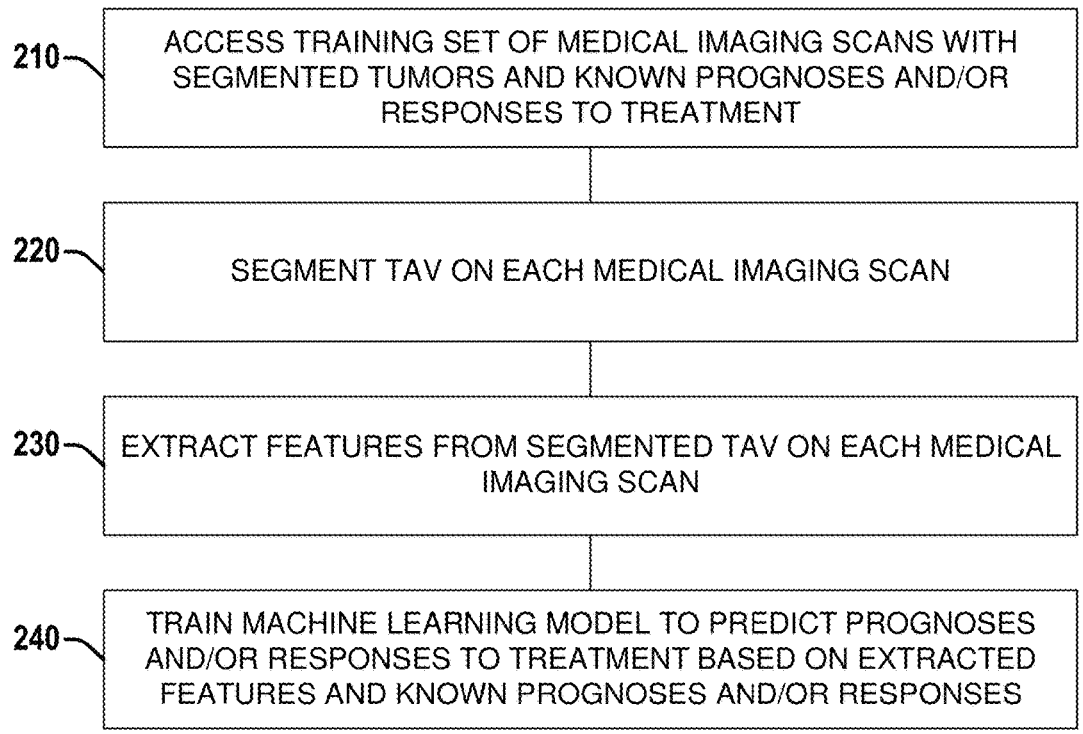
FIG. 2 illustrates a flow diagram of an example method/set of operations that can be performed by one or more processors to construct a model to determine a therapy response and/or prognosis of a tumor based at least in part on morphological, spatial organization, and/or functional features of tumor-associated vasculature (TAV), according to various aspects discussed herein.

Referring to FIG. 2, illustrated is a flow diagram of an example method/set of operations 200 that can be performed by one or more processors to construct a model to determine a therapy response and/or prognosis of a tumor based at least in part on morphological, spatial organization, and/or functional features of tumor-associated vasculature (TAV), according to various aspects discussed herein.

The set of operations 200 can comprise, at 210, accessing a training set of medical imaging scans, wherein each medical imaging scan of the training set comprises an associated tumor (e.g., segmented on the scan or as described herein) associated with a known treatment response and/or prognosis for that medical imaging scan. In various embodiments and in the example use cases discussed below, the imaging scans can be obtained via a system and/or apparatus implementing the set of operations 200, or can be obtained from a separate medical imaging system (e.g., MRI system). Additionally, the image volume can be accessed contemporaneously with or at any point prior to performing the set of operations 200.

The set of operations 200 can further comprise, at 220, for each medical imaging scan of the training set, segmenting associated tumor-associated vasculature (TAV) for the associated tumor of that medical imaging scan.

The set of operations 200 can further comprise, at 230, for each medical imaging scan of the training set, extracting associated values for a set of features from the associated TAV for the associated tumor of that medical imaging scan.

The set of operations 200 can further comprise, at 240, training a machine learning model based on the associated values extracted from the associated TAV for the associated tumor of each medical imaging scan and on the associated at least one of the known response to the treatment or the known prognosis.

Additionally, or alternatively, set of operations 200 can comprise one or more other actions discussed herein in connection with constructing a model to determine a therapy response and/or prognosis of a tumor based at least in part on morphological, according to various aspects discussed herein.

Additional aspects and embodiments are discussed below in connection with the following example use cases.

Example Use Cases 1 and 2: Radiomic Measurements of Tumor-Associated Vasculature Morphology and Function on Pretreatment Dynamic MRI Identifies Responders to Neoadjuvant Chemotherapy

Example Use Case 1

The following discussion provides example embodiments in connection with a first example use case involving determining response to neoadjuvant chemotherapy (NAC) based at least in part on vascular morphology and/or function.

Introduction: Angiogenesis is crucial to a tumor's growth and an important factor in therapeutic outcome. Although quantitative analysis of tumors on dynamic contrast enhanced (DCE) MRI can provide indirect characterization of a tumor's vascularization, direct computational analysis of the tumor-associated vessel network remains a promising, but under-explored potential marker of therapeutic response. For instance, surrounding vasculature with a convoluted 3-dimensional shape and poor blood flow may indicate a more aggressive tumor and poorly facilitate delivery of therapeutic agents. The first example use case presents a computational approach for the prediction of neoadjuvant chemotherapy (NAC) response using quantitative imaging features describing the morphology and function of tumor associated vasculature on pretreatment MRI.

Methods: 243 patients who received DCE-MRI scans prior to neo-adjuvant chemotherapy (NAC) at institution A [n=83], B [n=76], or one of nine other institutions as part of the ISPY1 Trial [n=84] were divided randomly into training (n=123) and testing (n=120) sets. 148 patients were HER2− and received neoadjuvant AC-T, while the 95 HER2+ patients were treated with TCHP (ISPY predates anti-HER2 therapy and HER2+ ISPY patients were excluded). 79 patients achieved pathological complete response [pCR, ypT0/is] following NAC. MRI exams were collected with a 1.5 or 3 Tesla scanner in the axial or sagittal plane. A baseline scan and 2-5 scans after injection of a gadolinium-based contrast agent with a median temporal resolution of 2.5 minutes were acquired. A portion of the tumor was manually delineated (e.g., segmented, etc.), then semi-automatically expanded to 3D. Vasculature was isolated from subtraction images with a specialized filtering approach to detect vessel-shaped objects. Features describing the 3D shape and architecture of the tumor-associated vessel network (e.g., curvature, torsion, local orientation, etc.) and functional semi-quantitative pharmacokinetic (PK) measurements of temporal contrast enhancement changes (e.g., signal enhancement ratio, time to peak enhancement, rates of uptake and washout, etc.) were calculated (various embodiments can employ various functional measures, such as TAV function feature(s) measuring the dynamics of a contrast agent in the tumor and/or TAV, including one or more of a signal enhancement ratio, a time to peak enhancement, a rate of uptake, or a rate of washout. Additionally or alternatively, one or more parameters from fully quantitative pharmacokinetic modeling can be employed, such as $K_{trans}$, $V_e$, $V_p$, etc.). Performance was assessed by AUC (area under the ROC (receiver operating characteristic) curve), as well as the accuracy, sensitivity, and specificity at the operating point corresponding to the Youden Index (e.g., the point on the corresponding to the maximum value of Youden's J statistic, etc.). The most discriminating features were determined based on frequency of selection by the random forest classifier.

Results: Within the training set, PK parameters of the vessels (AUC=0.66) outperformed relative to the PK of tumor (AUC=0.63) and the PK of peritumoral regions (AUC=0.64); however, a combination of the three yielded the best performance (AUC=0.75). Vessel shape features alone achieved AUC=0.67 in the training set. When multi-region PK features and tumor shape features were combined and applied to the 120-patient independent testing set, the random forest classifier achieved an AUC of 0.70 and identified 81% of patients who would achieve pCR. Non-pCR was best characterized by increased vessel curvature and PK parameters indicating poor perfusion, such as greater time to peak enhancement, slower uptake rate, and quicker washout. The results of the first example use case are summarized in Table 1, below:

TABLE 1

Results of the First Example Use Case

|  | Accuracy (%) | Sensitivity (%) | Specificity (%) |
|---|---|---|---|
| Full Testing set (n = 120) | 67 | 81 | 60 |
| HER2+ (n = 44) | 70 | 95 | 48 |
| HER2− (n = 76) | 64 | 63 | 65 |
| HER2−, HR+ (n = 51) | 67 | 83 | 64 |
| Triple Negative (n = 25) | 60 | 50 | 67 |

Conclusions: The findings of the first example use case suggest that properties of the tumor-associated vessel network, such as its shape and enhancement profile, can provide value in identifying patients who will respond to NAC before administration of treatment.

Example Use Case 2

The following discussion provides example embodiments in connection with a second example use case involving determining response to NAC based at least in part on vascular morphology and/or function.

Introduction: Angiogenesis is crucial to a tumor's growth and an important factor in therapeutic outcome. Pharmacokinetic (PK) analysis of tumor enhancement on dynamic contrast enhanced (DCE) MRI can provide indirect characterization of a tumor's vascularization. Direct computational analysis of the tumor-associated vessel network remains a promising, but under-explored potential marker of therapeutic response. For instance, vasculature with a convoluted 3-dimensional (3D) shape and poor blood flow may indicate a more aggressive tumor and poorly facilitate delivery of therapeutic agents.

Objectives: Explore a computational approach for predicting neoadjuvant chemotherapy (NAC) response using quantitative imaging features describing the morphology and function of tumor-associated vasculature on pretreatment MRI.

Study Design: 243 patients who received DCE-MRI scans prior to NAC at University Hospitals [n=83], Cleveland Clinic [n=76], or one of nine other ISPY1 Trial institutions (4) [n=84] were divided randomly into training (n=123) and testing (n=120) sets. 148 patients were HER2− and received neoadjuvant AC-T, while 95 HER2+ patients received TCHP (HER2+ ISPY patients did not receive targeted NAC and were excluded). 79 patients achieved pathological complete response [pCR, ypT0/is] following NAC.

Figure 3:
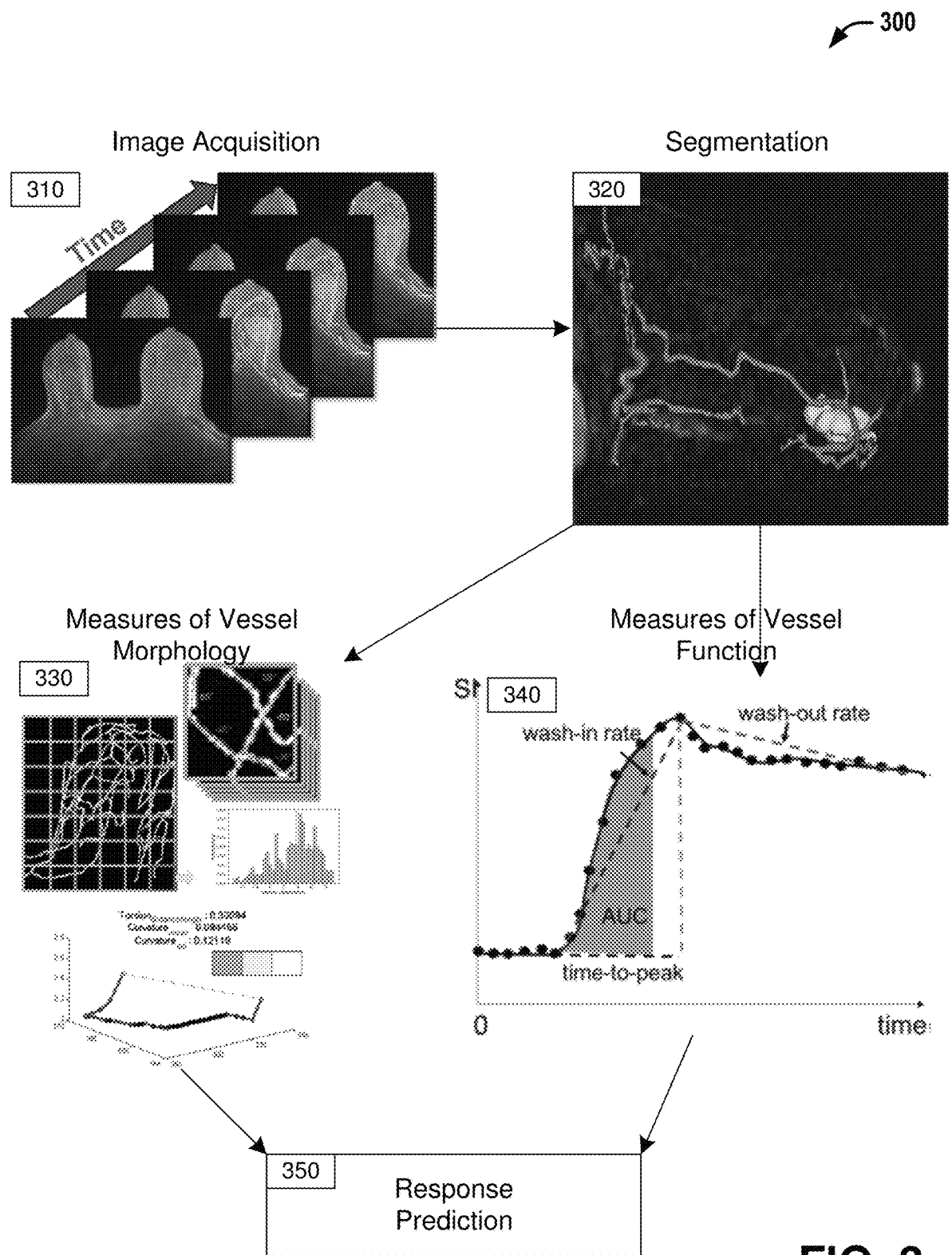
FIG. 3 illustrates a diagram showing the experimental framework employed in the second example use case, in connection with various aspects discussed herein.

Experimental Framework: Referring to FIG. 3, illustrated is a diagram showing the experimental framework 300 employed in the second example use case, in connection with various aspects discussed herein.

At 310, image acquisition was performed, which in the second example use case involved acquiring 1.5 or 3 Tesla MRI scans in the axial or sagittal plane, including baseline and 2-5 post-contrast scans (with median temporal resolution=2.5 min.).

At 320, segmentation was performed, which in the second example use case involved manual tumor annotations that were semi-automatically expanded to 3D, and vasculature that was isolated with a specialized filtering approach.

At 330, measures of vessel morphology were determined. In the second example use case, these measures comprised features of the shape and architecture of the tumor-associated vessels, for example vessel orientation feature(s) (which can measure heterogeneity of directional alignment of vessels), vessel tortuosity feature(s) (which can measure 3D twisting through metrics such as curvature and torsion), etc.

At 340, measures of vessel function were determined. In the second example use case, these measures comprised semi-quantitative pharmacokinetic (PK) voxel-wise measures of temporal intensity changes (e.g. uptake and washout rates, enhancement ratio, etc.), typically within a tumor, although the second example use case considered eight PK features in: (1) tumor, (2) peritumoral region, and (3) tumor-associated vasculature.

At 350, a NAC response (e.g., pCR or non-pCR) was predicted. Feature groups were separately optimized to predict response in the training set, and a random forest (RF) classifier combining vessel morphology and function was applied to the prediction of NAC response within the testing set.

Results: Three experiments were conducted in connection with the second example use case: (1) vessel morphology associated with NAC response, (2) vessel function associated with NAC response, and (3) a combination of vessel morphology and function predicting response in the testing set.

Figure 4:
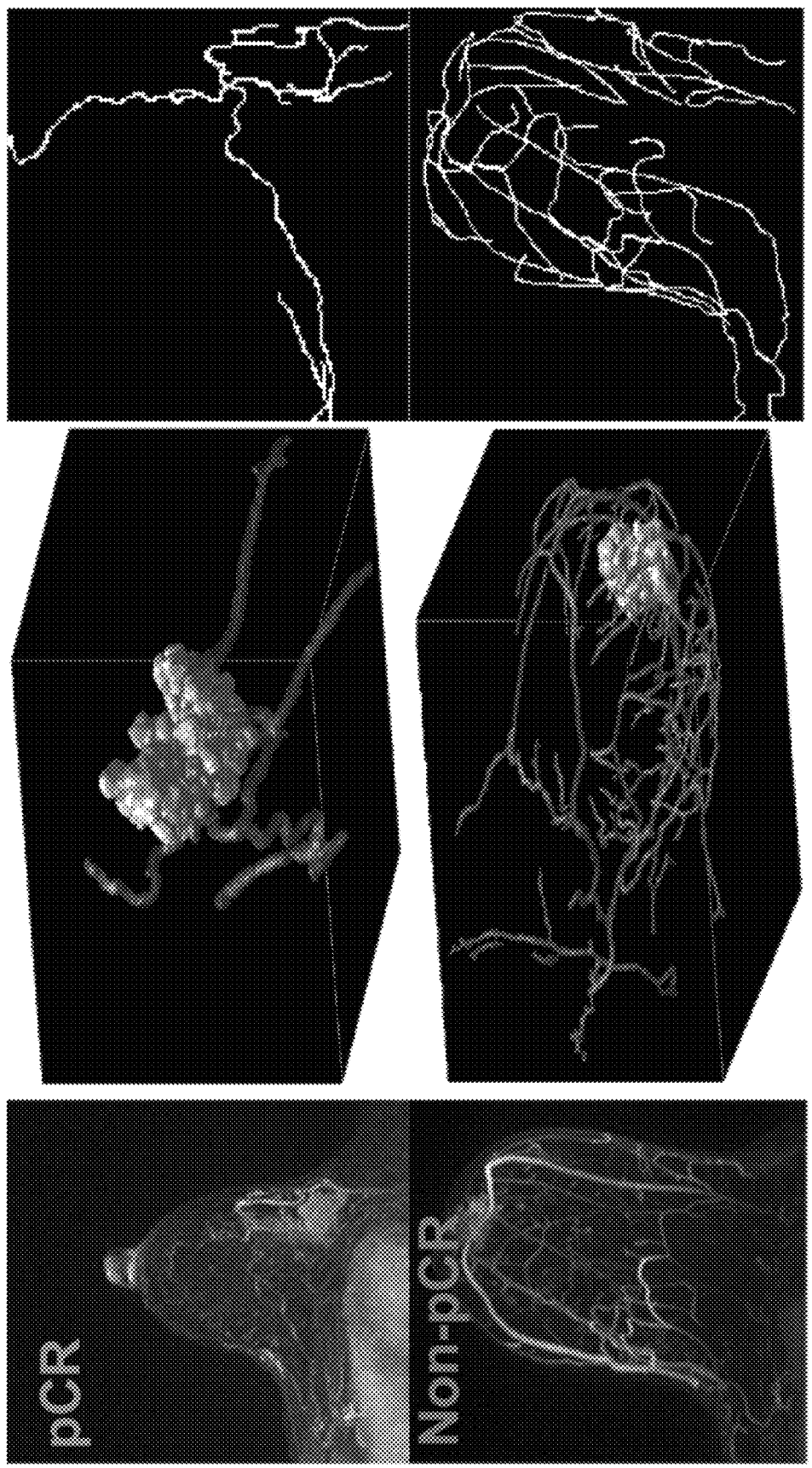
FIG. 4 illustrates example images of a scan (left images), segmented tumor and vasculature (center images), and vessels (right images) for pCR (top row) and non-pCR (bottom row) patients, in connection with various aspects discussed herein.

In the first experiment, the association between vessel morphology and NAC response was studied. Features of vessel shape up to 4.3 cm from the tumor achieved best response prediction results of features studied on the training set, and the top features found were orientation heterogeneity in the XY plane and curvature. These features provided an AUC=0.67 in the training set. Referring to FIG. 4, illustrated are example images of a scan (left images), segmented tumor and vasculature (center images), and vessels (right images) for pCR (top row) and non-pCR (bottom row) patients, in connection with various aspects discussed herein. As can be seen in FIG. 4, non-pCR exhibits greater heterogeneity of vessel orientations in the XY plane, whereas pCR vasculature has greater direction regularity.

Figure 5:
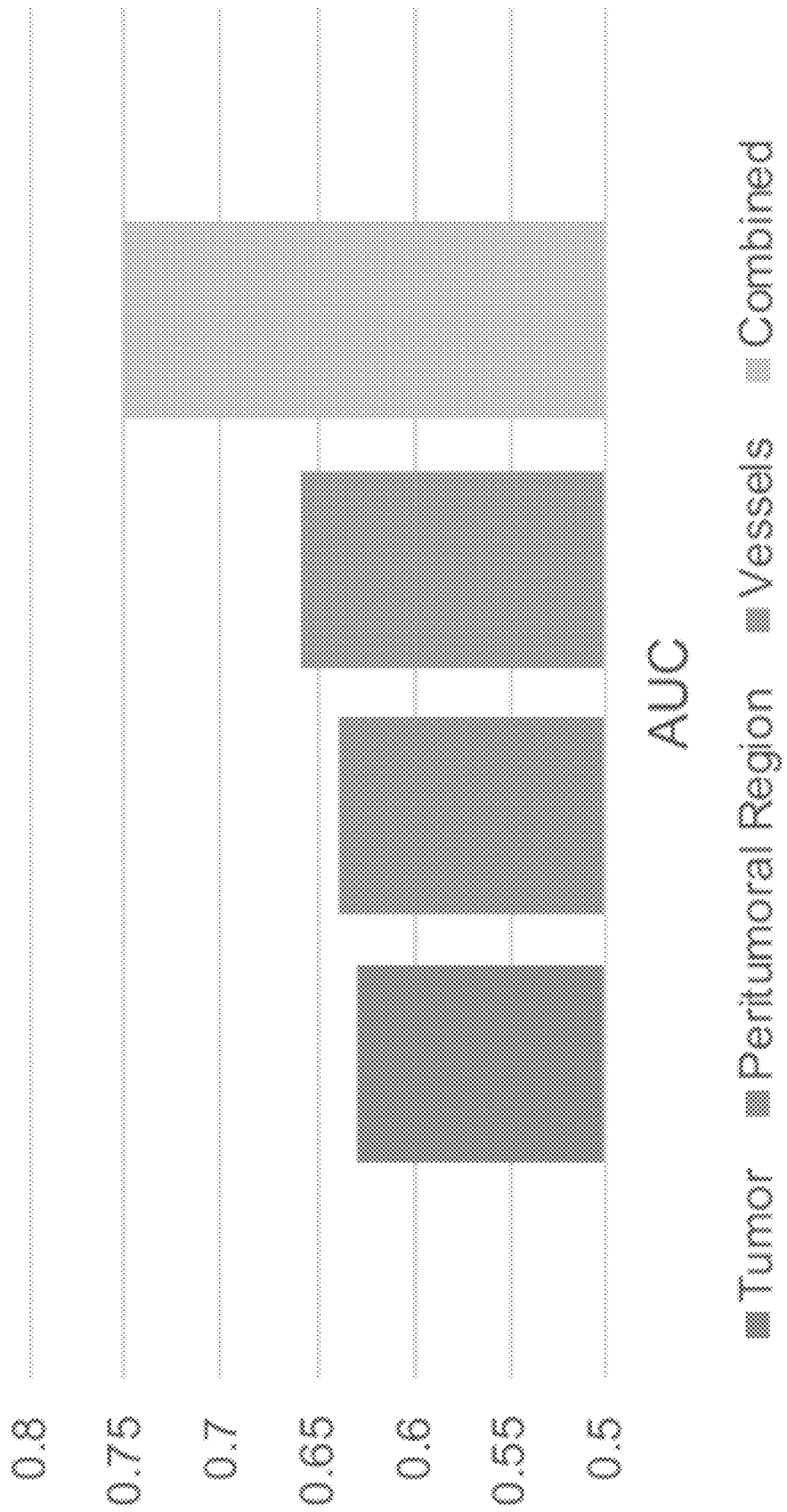
FIG. 5 illustrates a graph showing PK (pharmacokinetic) feature set performance within each spatial region, and combined across all regions, in connection with various aspects discussed herein.

In the second experiment, the association between vessel function and NAC response was studied. Functional PK measures from 0.2-3.0 cm outside the tumor yielded the best training set results, and it was found that PK features of vessels outperformed tumoral and peritumoral measures. The top features determined on the training set in the second experiment comprised uptake rate, washout rate, and time to peak enhancement. Referring to FIG. 5, illustrated is a graph showing PK feature set performance within each spatial region, and combined across all regions, in connection with various aspects discussed herein.

Figure 6:
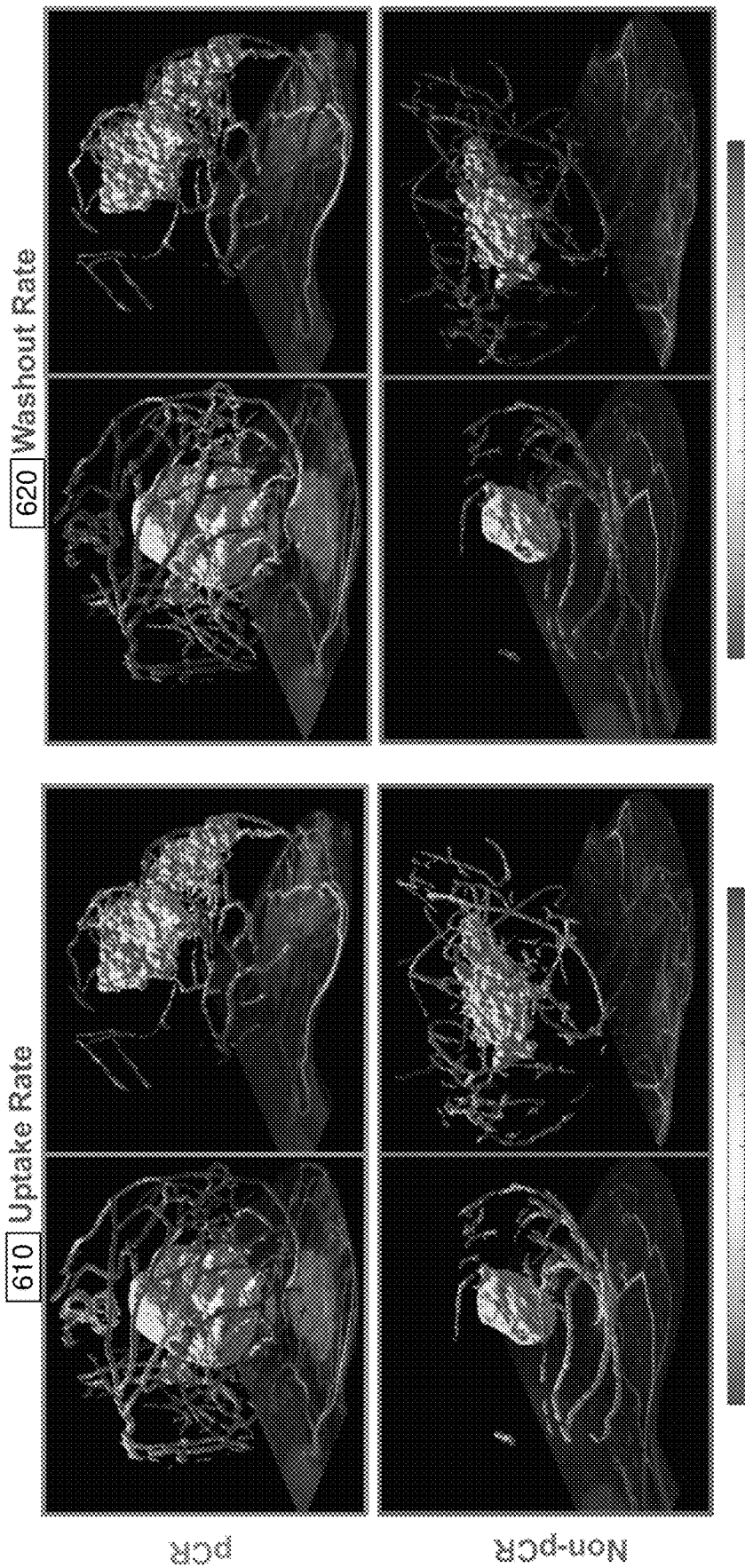
FIG. 6 illustrates example images showing uptake rate and washout rate for example pCR (top row) and non-pCR (bottom row) patients, in connection with various aspects discussed herein.

In the third experiment, the ability of a combination of vessel morphological and functional features to predict NAC response in the testing set was studied. Multi-region PK features and vessel shape features were combined into a random forest classifier (although other classifiers can be employed in various embodiments) and applied to the test set. The classifier achieved an AUC of 0.70 and identified 81% of patients who would achieve pCR. Referring to FIG. 6, illustrated are example images showing uptake rate (at 610) and washout rate (at 620) for example pCR (top row) and non-pCR (bottom row) patients, in connection with various aspects discussed herein. As can be seen in FIG. 6, non-responders were distinguished by greater architectural disorder and reduced function of vasculature. Compared to non-pCR, patients who achieved pCR showed (A) increased uptake rate (e.g., more positive, in red) and (B) increased washout rate (e.g., more negative, shown in blue) within the tumor vasculature.

Conclusions: The findings of the second example use case suggest that properties of the tumor-associated vessel network, such as its shape and enhancement profile, can provide value in identifying patients who will respond to NAC prior to administration of treatment and in monitoring treatment response.

Example Use Case 3: Computational Measurements of Tumor-Associated Vasculature Morphology on Clinical Imaging as a Predictive and Prognostic Biomarker of Treatment Response in Multiple Cancers The following discussion provides example embodiments in connection with a third example use case involving determining response to NAC based at least in part on vascular morphology and/or function.

Overview

The tumor-associated vasculature (TAV) differs from healthy blood vessels by its convolutedness, leakiness, and chaotic architecture, and these attributes facilitate the creation of a treatment resistant tumor microenvironment. Measurable differences in these attributes might also help identify patients who do and do not benefit from therapeutic intervention (e.g., chemotherapy). The third example use case presents a new computational image-based biomarker, quantitative tumor-associated vasculature (QuanTAV) features, and demonstrates its ability to predict response and survival across multiple cancer types, imaging modalities, and treatment regimens. The third example use case isolated tumor vasculature and extracted mathematical measurements of twistedness and organization from routine pre-treatment radiology (computed tomography or contrast-enhanced MRI) of a total of 558 patients, who received one of four first-line chemotherapy-based therapeutic intervention strategies for breast (n=371) or non-small cell lung cancer (NSCLC, n=187). Across four chemotherapy-based treatment strategies, classifiers of QuanTAV measurements significantly (p<0.05) predicted response in held out testing cohorts alone (AUC=0.63-0.71) and significantly improved models of clinical variables (AUC=0.70-0.85). Similarly, QuanTAV risk scores were derived that were prognostic of recurrence free survival in treatment cohorts who received surgery following chemotherapy for breast cancer (p=0.0022, HR=1.25, 95% CI 1.08-1.44, C-index=0.66) and chemoradiation for NSCLC (p=0.039, HR=1.28, 95% CI 1.01-1.62, C-index=0.66), as well as categorical TAV high/low risk groups that were independently prognostic among all treatment groups, including stratifying NSCLC patients who received chemotherapy only by progression-free survival (p=0.034, HR=2.29, 95% CI 1.07-4.94, C-index=0.62). In all cases, TAV response and risk scores were independent of clinicopathological risk factors and matched or exceeded models of clinical variables including post-treatment response. Across these domains, an association was observed between vascular morphology on CT and MRI—as indicated by elevated vessel curvature, torsion, and heterogeneity of orientation—and treatment outcome, suggesting the potential of TAV shape and structure as a novel pan-cancer prognostic and predictive non-invasive biomarker.

Introduction

Neoadjuvant chemotherapy (NAC), or chemotherapy administered prior to surgical intervention, often constitutes first-line intervention in a number of cancer domains. When successful, NAC can offer substantial benefits for patients by reducing tumor burden and increasing a patient's surgical options. However, many patients ultimately fail to respond and experience harmful side effects without benefit. Furthermore, in many cancers, including breast and non-small cell lung cancer (NSCLC), there is a current lack of validated predictive and prognostic biomarkers capable of definitively guiding first-line chemotherapeutic interventions.

Neovascularization and tumor angiogenesis have long been shown to be crucial in cancer progression, both local and metastatic spread. Through influence over the body's machinery for synthesizing new vasculature, a tumor will initiate the formation of new blood vessels in the surrounding peritumoral environment. This newly formed vessel network, known as tumor-associated vasculature (TAV), enables tumor growth by perfusing it with oxygen and nutrients, as well as providing an avenue for metastatic spread. Histological and molecular evidence of elevated tumor angiogenesis, such as increased density of microvessels measured via immunostaining or elevated vascular endothelial growth factor (VEGF) expression, has been shown to indicate poorer prognosis and therapeutic response. However, a critical aspect of tumor angiogenesis not captured by such approaches is with regard to abnormalities in the architecture of the resultant vasculature. The TAV possesses crucial architectural differences from healthy blood vessels: excessive up-regulation of angiogenesis creates vessels that are twisted, leaky, and chaotically organized. This aberrant vessel morphology has also been implicated in potentiating treatment refractoriness by reducing drug transfer to the tumor bed, thus leading to a lack of durable response. Conversely, successful normalization of TAV architecture can promote the efficacy of therapeutic intervention. It is likely that tumors that are resistant to chemotherapeutic intervention will differ in the twistedness and arrangement of their vasculature relative to responsive tumors, which in turn can be captured quantitatively on radiologic imaging.

Previous work has shown that morphology of the TAV on radiologic scans such as CT and MRI is important in cancer diagnosis. Consequently, computerized analysis of TAV twistedness and organization might provide an effective means of identifying patients who will benefit from NAC.

The third example use case presents a new computational image biomarker based on quantitative tumor-associated vasculature (QuanTAV) measurements that characterize the morphology and architecture of the vessel network surrounding a tumor on radiology scans. The third example use case also presents and evaluates a number of computationally extracted measurements of TAV twistedness and organization on pre-treatment contrast-enhanced magnetic resonance imaging (MRI) of breast cancer patients and computed tomography (CT) of lung cancer patients. The predictive and prognostic utility of the QuanTAV features were further demonstrated in the context of response to chemotherapy-related treatments for four use cases involving breast and lung cancers on two different imaging modalities—CT and MRI. In total, the prognostic and predictive utility of QuanTAV was evaluated on 558 patients, including 242 breast cancer patients receiving anthracycline-based NAC [BRCA-ACT], 129 breast cancer patients receiving HER2-targeted NAC [BRCA-TCHP], 97 NSCLC patients receiving platinum-based chemotherapy without surgery [NSCLC-PLAT], and 90 NSCLC patients receiving a trimodality regimen of neoadjuvant chemoradiation followed by surgical intervention [NSCLC-TRI]. Patients received standard imaging for their cancer setting: dynamic contrast-enhanced (DCE) MRI in breast cancer and standard dose chest computed tomography (CT) in NSCLC. Computer vision and image processing tools were employed for the segmentation of tumors and tumor-associated vasculature on MRI and CT scans, from which quantitative metrics of vessel network morphology and organization were computed. For each treatment group, TAV response and risk scores were derived from these metrics, then their ability to predict response and time to recurrence or progression was evaluated.

Results

A Framework for Quantifying the Twistedness and Organization of the Tumor-Associated Vascular Network From pre-treatment imaging, the TAV was extracted and its morphology and organization were characterized in order to predict therapeutic outcome. Tumor boundaries were first identified with a combination of manual and semi-automated approaches. The TAV was then segmented through a specialized filtering approach to emphasize vessel-like objects, and then refined through morphological processing and manual adjustment. Segmented vessels were then divided into constituent branches and reduced to centerline skeletons by a fast marching algorithm. From vessel centerlines, a set of 91 QuanTAV measurements were computed, belonging to one of two categories:

QuanTAV morphology (61 features): Features describing the 3D shape of tumor vessels. Metrics measuring the twistedness of vessels across different length scales were computed: torsion, measuring twistedness across a full vessel branch, and curvature, measuring local twistedness among adjacent points along a branch. First order statistics describing the distribution of these measures between vessel branches and the entire vasculature are computed. Additional metrics such as the volume and length of the TAV, as well as the proportion of vessels entering a tumor, are also computed. TAV morphology features are listed in full in Table 2, below.

TABLE 1

Full list of 61 QuanTAV Morphology features extracted

| Features | Description |
| --- | --- |
| Statistics of torsion per branch (f1-f5) | Mean, standard deviation (std), maximum (max), skewness (skew), and kurtosis (kurt) of torsion across all branches |
| Statistics of curvature standard deviation per branch (f6-f10) | Mean, std, max, skew, kurt of the standard deviation of curvature measured along each branch |
| Statistics of mean curvature per branch (f11-f15) | Mean, std, max, skew, kurt of the average curvature measured along each branch |
| Statistics of maximum curvature per branch (f16-f20) | Mean, std, max, skew, kurt of the maximum curvature measured along each branch |
| Statistics of curvature skewness per branch (21-f25) | Mean, std, max, skew, kurt of the skewness of curvature measured along each branch |
| Statistics of curvature kurtosis per branch (f26-f30) | Mean, std, max, skew, kurt of the kurtosis of curvature measured along each branch |
| Statistics of global vascular curvature (f31-f35) | Mean, std, max, skew, kurt of the curvature measured across all branches combined |
| Histogram of global vascular curvature (f36-f45) | 10-bin histogram of the curvature measured across all points of the vessel volume |
| Histogram of torsion (f46-f55) | 10-bin histogram of the torsion measured across all branches combined |
| Total vessel volume (f56-f58) | Vessel volume (f56), vessel volume normalized to the total size of the 3D region of interest (f57), vessel volume normalized to the volume of the tumor (f58). |
| Total vessel length (f59) | Total length of vessels within the region of interest |
| Tumor feeding branches (f60, f61) | Number (f60) and percentage (f61) of vessel branches that enter the tumor volume from the surrounding tumor environment. |

QuanTAV Spatial Organization (30 features): Features quantifying the degree of heterogeneity in the architecture of the tumor vasculature. 2D projections of the TAV are generated across each dimension of the imaging plane and in a spherical coordinate system relative to the tumor centroid within a fixed radius of the tumor. The set of QuanTAV Spatial Organization features is a set of statistics describing vessel orientations across each projection image. TAV organization features are listed in full in Table 3, below.

TABLE 3

Full list of 30 QuanTAV Spatial Organization features extracted.

| Features | Description |
| --- | --- |
| Statistics of vessel orientation along XY projection image (f1-f5) | Mean, median (med), standard deviation (std), skewness (skew), and kurtosis (kurt) of local vessel orientations computed across XY vessel map |

TABLE 3-continued

Full list of 30 QuanTAV Spatial Organization features extracted.

| Features | Description |
| --- | --- |
| Statistics of vessel orientation along the XZ projection image (f6-f10) | Mean, med, std, skew, kurt of local vessel orientations computed across XZ vessel map |
| Statistics of vessel orientation along the YZ projection image (f11-f15) | Mean, std, max, skew, kurt of local vessel orientations computed across XZ vessel map |
| Statistics of vessel orientation along the rotation-elevation projection image (f16-f20) | Mean, std, max, skew, kurt of local vessel orientations computed across vessel map of rotation and elevation with respect to the tumor |
| Statistics of vessel orientation along the distance-rotation projection image (21-f25) | Mean, std, max, skew, kurt of local vessel orientations computed across vessel map of distance and rotation with respect to the tumor |
| Statistics of vessel orientation along the distance-elevation projection image (f26-f30) | Mean, std, max, skew, kurt of local vessel orientations computed across vessel map of distance and elevation with respect to the tumor |

Figure 7:
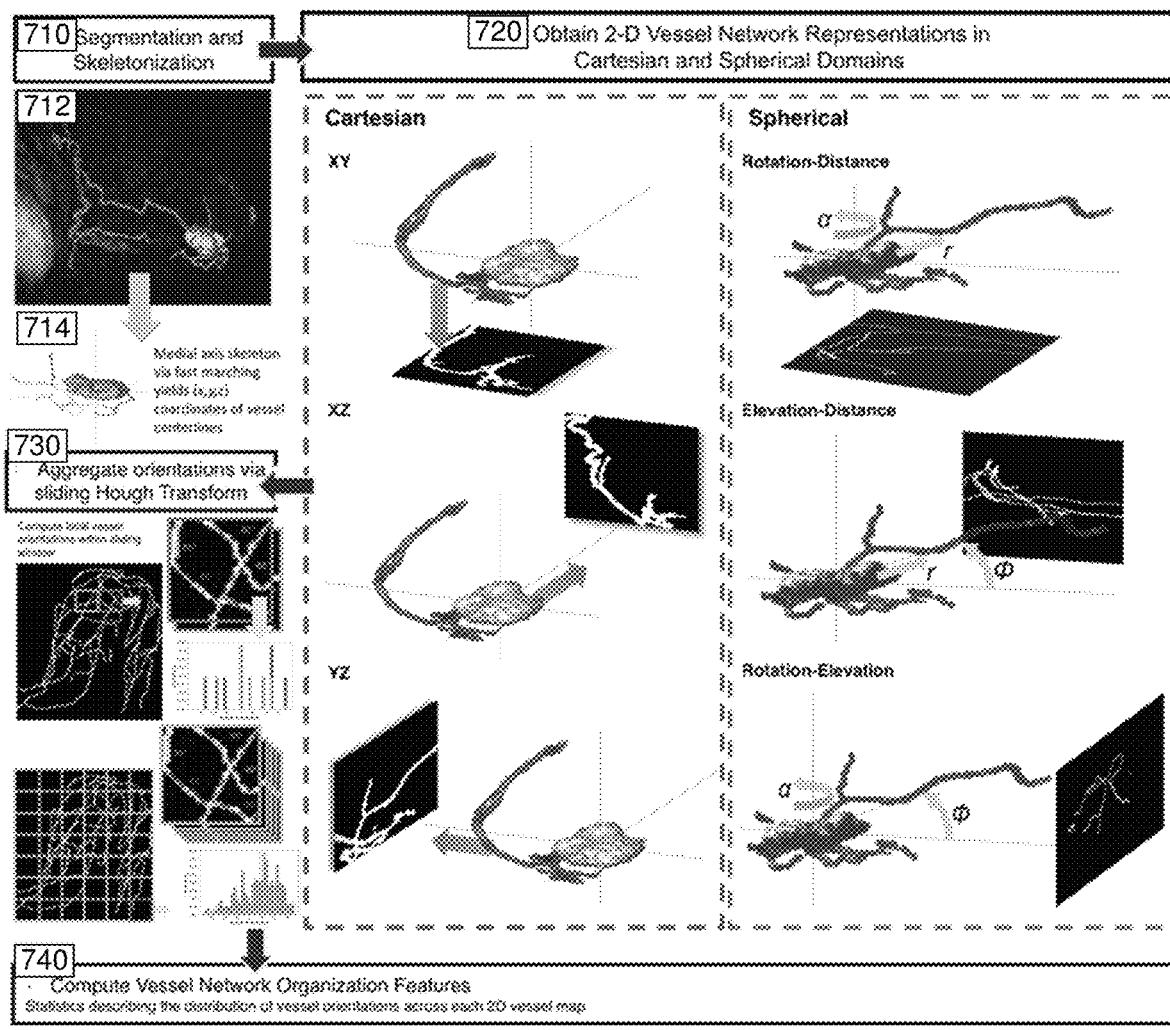
FIG. 7 illustrates images showing the workflow employed in the third example use case for computing features describing tumor-associated vasculature organization, in connection with various aspects discussed herein.

Referring to FIG. 7, illustrated are images showing the workflow employed in the third example use case for computing features describing tumor-associated vasculature organization, in connection with various aspects discussed herein. QuanTAV Spatial Organization features quantify the distribution of local vessels within a fixed radius surrounding the tumor by creating 2D projection images of a vessel's position in cartesian (X,Y,Z) space and spherical (rotation and elevation relative to the tumor surface, and distance relative to the tumor surface). Each project image was then analyzed locally within a sliding window. The Hough transform was applied to detect lines within the window and quantify their orientation. The most prominent vessel orientations, up to a maximum of five (various embodiments can employ a different maximum), were stored. Statistics of the distribution of vessel orientations form the set of TAV organization features. The maximum distance from the tumor and size of the sliding window were optimized for each cancer domain/imaging modality by performance of a classifier in cross-validation in the training sets.

Each treatment group was randomly split into training and testing sets and analyzed separately according to the following procedure. First, computer-extracted QuanTAV measurements were explored as a predictive marker of therapeutic response. QuanTAV features were optimized for each imaging modality, and then used to derive a QuanTAV response score. Feature selection was performed to obtain a minimal signature of QuanTAV features most associated with therapeutic response, which was then used to train a linear discriminant analysis (LDA) classifier to predict probability of therapeutic response. Across four therapeutic strategies in breast (BRCA-ACT and BRCA-TCHP) and lung cancer (NSCLC-PLAT and NSCLC-TRI), QuanTAV response scores were derived in this fashion and their association with established clinical response endpoints was assessed in the independent testing cohorts. Clinical variables found to be significantly associated with response in a univariate setting within the training set were incorporated into comparative clinical models, as well as combined with QuanTAV response scores to assess the benefit and multivariate significance of vascular analysis. Second, QuanTAV features were utilized to derive prognostic QuanTAV risk scores that could significantly distinguish time to recurrence or progression following multiple treatments in breast and lung cancer and assessed in a multivariable setting when combined with other clinical, radiologic, and pathologic information, including response following the completion of treatment.

Figure 8:
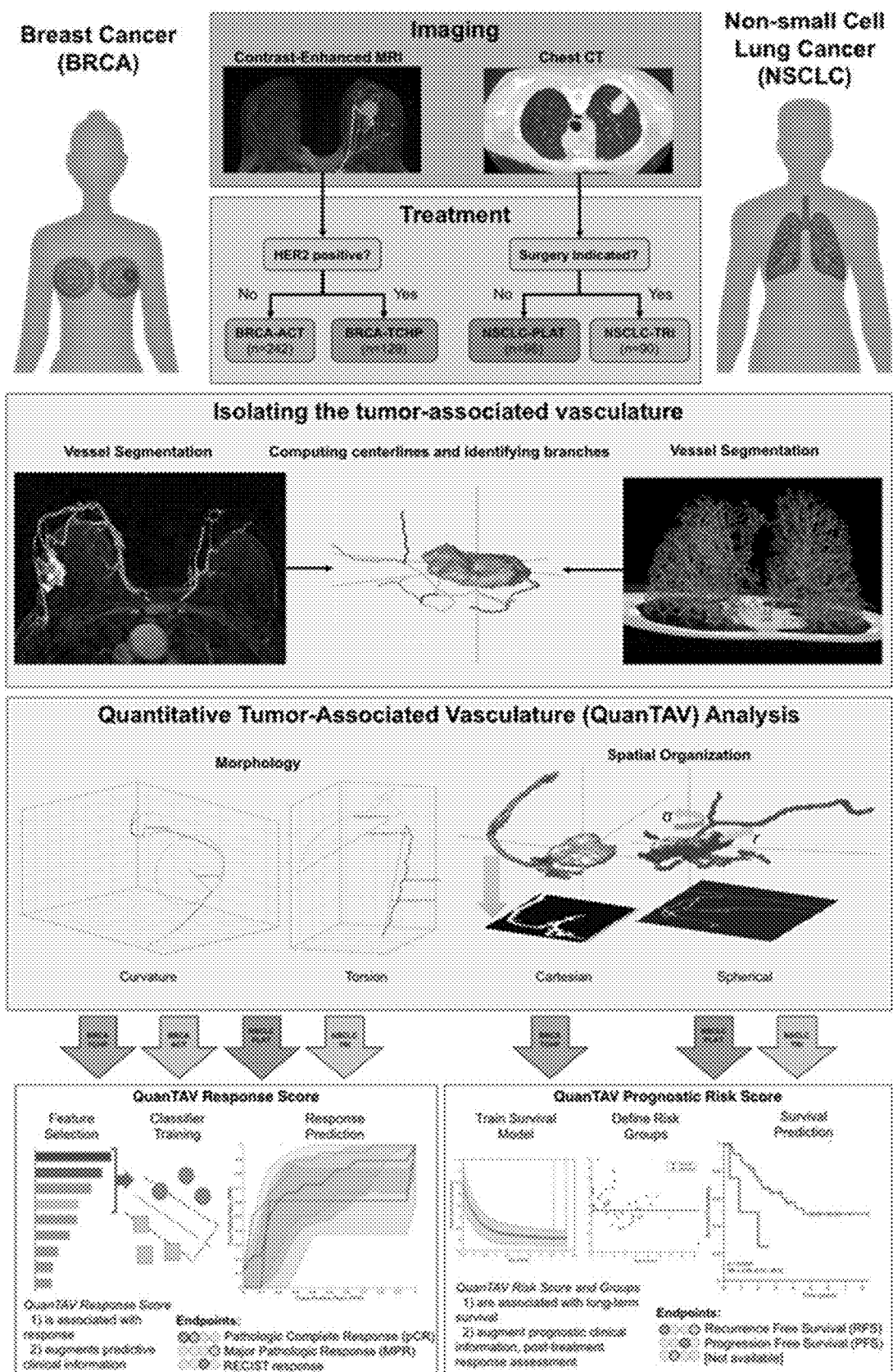
FIG. 8 illustrates example images and graphs showing an overview of the development and validation of tumor-associated vasculature (TAV) response and risk scores, in connection with various aspects discussed herein.

Referring to FIG. 8, illustrated are example images and graphs showing an overview of the development and validation of tumor-associated vasculature (TAV) response and risk scores, in connection with various aspects discussed herein. Models were trained and validated in four therapeutic cohorts: (a) anthracycline-based neoadjuvant chemotherapy [BRCA-ACT] and (b) neoadjuvant chemotherapy with anti-HER2 agents [BRCA-TCHP] in breast cancer and (c) platinum-based chemotherapy only [NSCLC-PLAT] and (d) neoadjuvant chemoradiation with surgery [NSCLC-TRI] in non-small cell lung cancer. The tumor and associated-vasculature were extracted from pre-treatment breast DCE-MRI and chest CT. For each vessel network, centerlines were derived and two categories of QuanTAV features were computed: Morphology and Organization. QuanTAV morphology features quantified the shape of tumor vessels. Statistics describing the distribution of metrics such as curvature (inversely proportional to the radius of a circle fitting three adjacent vessel points) and torsion (detecting differences in vessel length relative to the distance between its start and end points) comprised the bulk of QuanTAV morphology features. QuanTAV Spatial Organization features evaluate the architecture of the vessel network by evaluating the degree of vessel alignment along 2D projection images depicting the position of vessels in either the imaging space (Cartesian) or a coordinate system relative the tumor center and surface (spherical). QuanTAV features were optimized to predict response in each training cohort, then a linear discriminant analysis (LDA) classifier was trained to predict response from a limited set of features selected by Wilcoxon rank sum test (various embodiments can employ the same or other types of machine learning models). The output of the LDA classifier was a QuanTAV response score, which was assessed for ability to predict therapeutic response and multivariable significance in the testing set. Likewise, in the three cohorts with progression—(NSCLC-PLAT) or recurrence-free survival (BRCA-ACT, NSCLC-TRI) data available for a proportion of patients, a regularized cox proportional hazards model was trained to derive a QuanTAV risk score and corresponding risk groups in the training set, which were assessed for univariable and multivariable association with survival in the testing set.

Predicting Response and Recurrence for Anthracycline-Based NAC (BRCA-ACT) from Pre-Treatment Breast MRI For the majority of breast cancer patients who receive neoadjuvant treatment, a chemotherapy-only regimen followed by surgery is standard-of-care. A multi-institutional cohort of 242 patients who received anthracycline-cyclophosphamide alone or followed by a taxane (BRCA-ACT) was assembled. All BRCA-ACT recipients were negative for the HER2 receptor. 19.8% achieved pathologic complete response (pCR), defined as a lack of remaining invasive cancer cells within the breast or axilla based on pathological examination of excised surgical samples (ypT0/isN0), the most commonly utilized therapeutic endpoint in the breast NAC setting. A training cohort of 98 patients was used for model training ($D_{tr}^1$), and the remaining 144 patients were reserved for independent testing ($D_{te}^1$). Within $D_{tr}^1$, parameters related to the computation of QuanTAV features were optimized for performance. Within cross-validation, the set of features most discriminative of pCR were selected and used to train a linear discriminant analysis (LDA) classification model.

Figure 9:
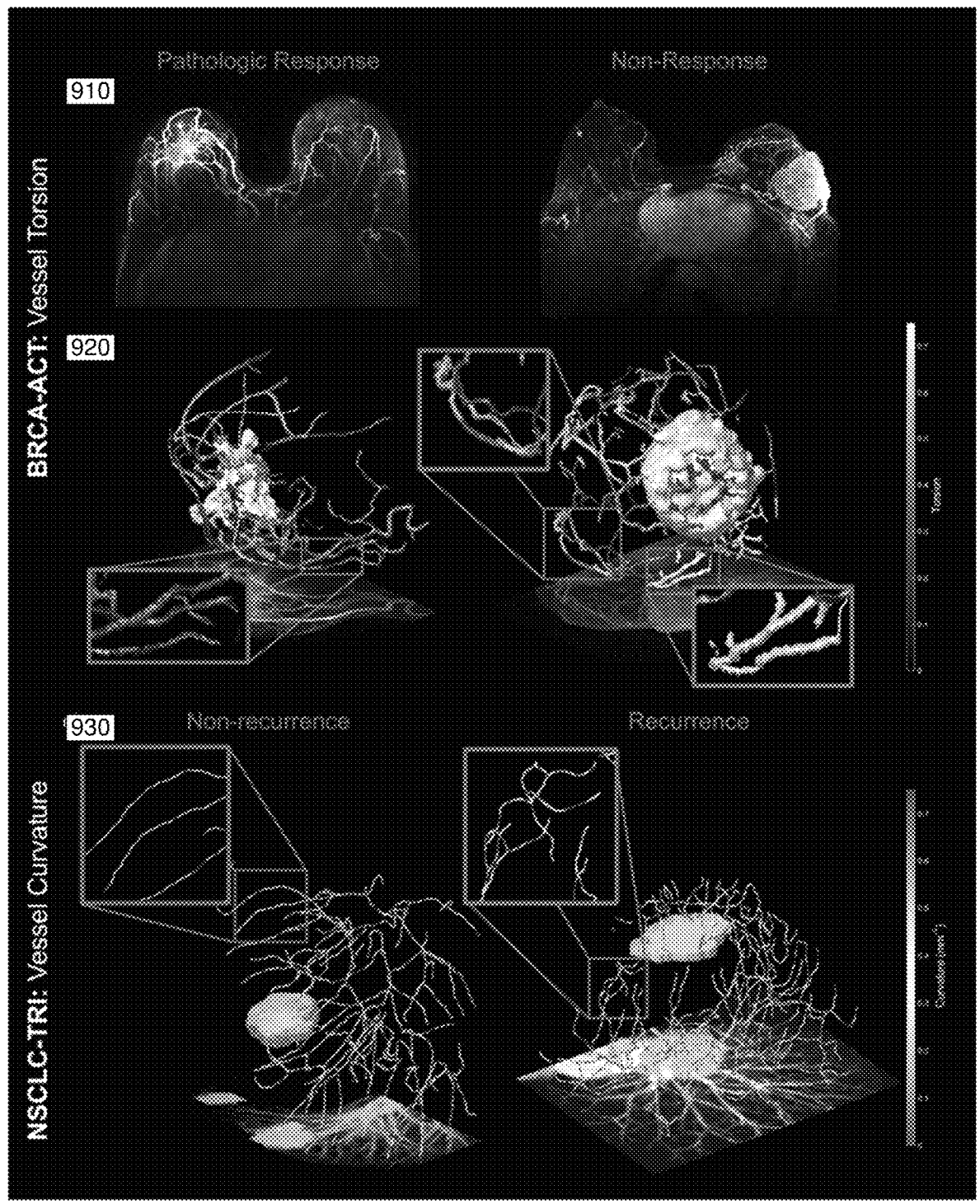
FIG. 9 illustrates example images showing how QuanTAV (quantitative TAV) morphology measures detect differences in vessel shape on pre-treatment breast MRI and lung CT predictive of outcome following treatment including chemotherapy, in connection with various aspects discussed herein.

Referring to FIG. 9, illustrated is a series of example images showing how QuanTAV morphology measures detect differences in vessel shape on pre-treatment breast MRI and lung CT predictive of outcome following treatment including chemotherapy, in connection with various aspects discussed herein. At the top of FIG. 9 (910 and 920), Elevated vessel torsion is associated with non-response to anthracycline-based chemotherapy in breast cancer (BRCA-ACT). Images 910 show maximum intensity projections of pre-treatment DCE-MRI subtraction images for patients who did (left) and did not (right) experience pathologic complete response (pCR) following BRCA-ACT. Images 920 show vessel torsion on pre-treatment dynamic MRI distinguishes non-responders and complete responders (pCR). For each discrete vascular branch, all corresponding voxels within the branch are shaded according to the torsion value of the branch. The vasculature of patients who do not respond (left) exhibited elevated torsion, indicating vessels that twist back on themselves and are more convoluted in shape. Conversely, patients who achieve pCR exhibit less tortuous vasculature that transports blood more directly towards the tumor or throughout the breast. At the bottom of FIG. 9, 930 shows curvature across vessels on pre-treatment CT differs between NSCLC patients who will (right) and will not (left) recur following neoadjuvant chemoradiation followed by surgery (NSCLC-TRI). Vessel center-lines are shaded according to local curvature, computed for every set of three adjacent points along a vessel. Elevated standard deviation of curvature was associated with recurrence following NSCLC-TRI, visible as regions of local bends and twists along the length of a vessel (right). Responsive patients, in contrast, were surrounded by vessels with fewer of these micro-deviations.

An increase in average torsion across vessels was the feature most strongly associated with failure to achieve complete response (e.g., as seen at 910 and 920 for BRCA). Defined as the complement of the ratio of the Euclidean distance between the start and end points of a vessel and its total length, torsion was found to be elevated in vessels with internal looping or "U"-shaped vessels that terminate near their origin. Due to such patterns, tortuous vessels in non-pCR patients (920, right image) reflect lower spatial efficiency, diverging from healthy breast vasculature where vessels originate from thoracic and intercostal vessels and radiate and perforate regularly across the breast.

An LDA classifier incorporating 6 QuanTAV features (see Table 4, below) achieved the best performance in $D_{tr}^1$ with a cross-validated area under the receiver-operating characteristic curve (AUC) of 0.62. When applied to $D_{te}^1$, QuanTAV response scores obtained from the LDA classifier identified pCR with AUC=0.65 (95% CI 0.54-0.76, p=0.009) and was independently significant in a multivariable comparison with clinic-pathologic variables (see FIG. 10, discussed below). Of three available clinical parameters (age, size, and hormone receptor positivity), only hormone receptor positivity had univariate significance in $D_{tr}^1$. A Cox proportional hazards model combining this variable and QuanTAV response score yielded an AUC=0.78 (95% CI 0.63-0.87, p=2e-5) in $D_{te}^1$, an increase over hormone receptor status only (AUC=0.69, 95% CI 0.58-0.80, p=0.0316). When compared with all clinical variables in $D_{te}^1$, QuanTAV response score was found to be independently associated with response with an odds ratio (OR) of 0.02 (95% CI 0.00-0.32, p=0.005), along with hormone receptor positivity and age.

Table 4 shows the top features and corresponding coefficients for the LDA classifier to predict pCR in HER2– breast cancer patients receiving anthracycline-based NAC, derived in a n=98 training set. Expression of features with positive coefficients contributes to a response prediction, while expression of features with negative coefficients contributes to a prediction of non-response.

TABLE 4

Top features and corresponding coefficients for LDA classifier to predict pCR in HER2– breast cancer patients receiving anthracycline-based NAC

| Feature Name | Coefficient |
| --- | --- |
| QuanTAV Spatial Organization - YZ - Skewness | 0.18 |
| QuanTAV Spatial Organization - Distance-Elevation - Median | 0.72 |
| QuanTAV Spatial Organization - Distance-Elevation - Mean | −0.16 |
| QuanTAV Spatial Organization - XZ - Skewness | 0.060 |
| QuanTAV Spatial Organization - YZ - Median | 0.88 |
| QuanTAV - Torsion - Mean | −0.44 |
| Constant | −0.23 |

Referring to FIG. 10, illustrated are tables showing univariate (UVA) and multivariable (MVA) analysis of QuanTAV response score and available clinical variables for prediction of pCR to BRCA-ACT, in connection with various aspects discussed herein. Clinical variables that were individually significant in the training set (hormone receptor status) were incorporated into logistic regression models alone and with QuanTAV response score, and evaluated on the testing set.

157 BRCA-ACT recipients had 10-year recurrence-free survival (RFS) information available in addition to pathologic response. 48 patients experienced recurrence, with a median time to recurrence of 77.7 months. A Cox proportional hazards model with elastic net regularization was trained to derive a QuanTAV risk score via cross-validation in $D_{tr}^1$ (n=63), in turn comprised of 14 QuanTAV features (See Table 5, below). Additionally, a QuanTAV risk score threshold was derived from the training set to stratify patients into low- and high-risk groups. Performance of both risk score and groups in both training and testing are listed in Table 6, below. When applied to $D_{te}^1$ (n=93), QuanTAV risk score was significantly prognostic as both a continuous score (p=0.0022, HR=1.25, 95% CI 1.08-1.44, C-index=0.66) and categorical low- and high-risk groups (p=0.0096, HR=4.25, 95% CI 1.29-14.07, C-index=0.62). The QuanTAV model was independently prognostic in a multivariate setting as both a continuous risk score (p=0.0049) and categorical risk groups (p=0.019), along with the majority of clinical variables (See Table 7, below).

Table 5 shows the set of features selected by the elastic-net Cox regression model as being most prognostic of RFS from initiation of NAC among breast cancer patients receiving BRCA-ACT and their corresponding hazard ratios, derived within the n=44 patient training set. The hazard ratios shown here reflect the risk of an increase of one standard deviation in feature value on the training set. A hazard ratio of less than 1 implies that an increase in that feature's value is associated with reduced risk, while a hazard ratio greater than 1 implies the opposite.

TABLE 5

Most Prognostic Features for BRCA-ACT and Corresponding Hazard Ratios

| Feature Name | Hazard Ratio |
| --- | --- |
| QuanTAV Spatial Organization - Distance-Rotation - Skewness | 0.89 |
| QuanTAV Spatial Organization - Distance-Elevation - Standard Deviation | 0.89 |
| QuanTAV Spatial Organization - Rotation-Elevation - Skewness | 0.90 |
| QuanTAV Spatial Organization - Distance-Rotation - Standard Deviation | 0.93 |
| QuanTAV Spatial Organization - XZ - Kurtosis | 0.93 |
| Ratio of Vessel to Tumor Volume | 0.96 |
| QuanTAV Morphology - Torsion Histogram - Bin 2 | 0.98 |
| QuanTAV Spatial Organization - YZ - Skewness | 1.00 |
| QuanTAV Spatial Organization - YZ - Kurtosis | 1.03 |
| QuanTAV Morphology - Torsion - Mean | 1.03 |
| No. Vessels Feeding Tumor | 1.05 |
| QuanTAV Morphology - Torsion - Standard Deviation | 1.06 |

TABLE 5-continued

Most Prognostic Features for BRCA-ACT and Corresponding Hazard Ratios

| Feature Name | Hazard Ratio |
| --- | --- |
| QuanTAV Spatial Organization - Rotation-Elevation - Kurtosis | 1.08 |
| Percentage of Vessels Feeding Tumor | 1.11 |

Table 6 shows hazard ratio (HR), concordance index (C-index), and p-value of the HR for each prognostic model in the training and testing sets.

TABLE 6

HR, C-index, and p-value of HR for each model in training and testing sets

| Cohort | Signature | Training | | | Testing | | |
| --- | --- | --- | --- | --- | --- | --- | --- |
| | | HR | C-index | p | HR | C-index | p |
| BRCA-ACT | Risk Score | 1.43 | 0.7948 | <1e−5 | 1.25 | 0.66 | 0.002 |
| | Risk Groups | 2.96 | 0.70 | 0.004 | 4.25 | 0.62 | 0.018 |
| NSCLC-PLAT | Risk Score | 1.32 | 0.77 | 1.0e−5 | 1.12 | 0.61 | 0.14 |
| | Risk Groups | 4.01 | 0.71 | <1e−5 | 2.23 | 0.62 | 0.002 |
| NSCLC-TRI | Risk Score | 1.32 | 0.81 | 1.9e−5 | 1.28 | 0.66 | 0.039 |
| | Risk Groups | 19.5 | 0.74 | 4.5e−5 | 3.66 | 0.64 | 0.036 |

Table 7 shows Cox proportional hazard univariate (UVA) and multivariable (MVA) analysis of 10-year recurrence free survival (RFS) following BRCA-ACT treatment, including QuanTAV risk score and available clinical variables.

TABLE 7

Cox Proportional Hazard UVA and MVA analysis of 10-year RFS following BRCA-ACT treatment

| | UVA | | MVA Risk Score (Continuous) | | MVA Risk Groups (Categorical) | |
| --- | --- | --- | --- | --- | --- | --- |
| | Hazard Ratio (95% CI) | p | Hazard Ratio (95% CI) | p | Hazard Ratio (95% CI) | p |
| QuanTAV risk score (increase of 1) | 1.25 (1.08-1.44) | 0.0022 | 1.23 (1.06-1.41) | 0.0049 | — | — |
| TAV Risk Group (High vs. Low Risk) | 4.25 (1.29-14.07) | 0.018 | — | — | 5.31 (1.32-21.39) | 0.019 |
| Hormone receptor status (positive vs. negative) | 0.45 (0.22-0.95) | 0.036 | 0.24 (0.10-0.58) | 0.0014 | 0.26 (0.11-0.61) | 0.0019 |
| Age (per year increase) | 0.95 (0.92-0.99) | 0.017 | 0.93 (0.89-0.97) | 0.0012 | 0.93 (0.89-0.97) | 0.0008 |
| Largest lesion diameter (per mm increase) | 1.10 (1.00-1.22) | 0.062 | 1.03 (0.91-1.18) | 0.62 | 1.03 (0.90-1.18) | 0.63 |
| Functional Tumor Volume (per 10 cc increase) | 1.21 (1.07-1.36) | 0.0017 | 1.10 (0.98-1.24) | 0.096 | 1.14 (1.02-1.28) | 0.025 |
| Pathologic Response (pCR vs. non-pCR) | 0.17 (0.02-1.22) | 0.078 | 0.07 (0.01-0.55) | 0.011 | 0.09 (0.01-0.69) | 0.021 |

The third example use case sought to evaluate whether TAV morphology provided predictive information independent of functional measures of vascularity based on contrast enhancement on perfusion imaging, such as DCE-MRI. A first group reported that functional tumor volume (FTV), the volume of tumor that is actively vascularized according to thresholding of semi-quantitative pharmacokinetic parameters, was associated with RFS within the ISPY1 trial data, which also comprised a portion of the BRCA-ACT cohort. The third example use case compared against FTV, as computed by the first group and provided for the ISPY1 trial and pilot datasets obtained through the cancer imaging archive.[36] FTV was significantly associated with RFS in $D_{te}^1$ (HR=1.20, 95% CI 1.11-1.31, p=1.7e-05) with a C-index of 0.67. In multivariate assessment also including the QuanTAV model and clinical variables (See Table 7, above), FTV remained significant when included with QuanTAV risk groups (p=0.0052), but not QuanTAV risk score (p=0.0813), whereas the QuanTAV risk score and groups were both significant. The third example use case further assessed the correlation between FTV and the features of the QuanTAV risk score (See Table 8, below). Eleven of fifteen risk-associated QuanTAV features were not significantly correlated with FTV (p>0.05). Unsurprisingly, the number (Pearson's correlation coefficient, p=0.23, p<0.026) and percentage of vessels feeding the tumor (p=0.54, p<1e-5), were significantly correlated with FTV. Additionally, two of the eight QuanTAV Spatial Organization features in the signature, skewness (p=−0.21, p=0.40) and standard deviation (p=−0.21, p=0.41) of the distance-rotation vessel map were significantly inversely correlated with FTV.

Table 8 shows correlation of features associated with RFS following BRCA-ACT treatment and significance before and after multiple comparison correction.

TABLE 8

Correlation of Features Associated with RFS following BRCA-ACT and p-value

| Feature Name | Correlation Coefficient | P-value |
| --- | --- | --- |
| QuanTAV Spatial Organization - XZ - Kurtosis | 0.0253 | 0.8086 |
| QuanTAV Spatial Organization - YZ - Skewness | −0.0392 | 0.7074 |
| QuanTAV Spatial Organization - YZ - Kurtosis | −0.1246 | 0.2315 |
| QuanTAV Spatial Organization - Rotation-Elevation - Skewness | 0.0006 | 0.9954 |
| QuanTAV Spatial Organization - Rotation-Elevation - Kurtosis | −0.1103 | 0.2900 |
| QuanTAV Spatial Organization - Distance-Rotation - Standard Deviation | −0.0843 | 0.4192 |
| QuanTAV Spatial Organization - Distance-Rotation - Skewness | −0.2126 | 0.0396 |
| QuanTAV Spatial Organization - Distance-Elevation - Standard Deviation | −0.2115 | 0.0407 |
| QuanTAV Morphology - Torsion - Mean | 0.0946 | 0.3645 |
| QuanTAV Morphology - Torsion - Standard Deviation | 0.1237 | 0.2348 |
| Ratio of Vessel to Tumor Volume | −0.1905 | 0.0660 |
| QuanTAV Morphology - Torsion Histogram - Bin 2 | −0.1549 | 0.1361 |
| No. Vessels Feeding Tumor | 0.2294 | 0.0262 |
| Percentage of Vessels Feeding Tumor | 0.5515 | <1E−5 |

Predicting Response to NAC with Targeted Therapy for HER2+ Breast Cancers (BRCA-TCHP) from Pre-Treatment MRI Breast cancers with overexpression of the HER2 surface protein are highly aggressive, but can often be effectively combated through a targeted NAC strategy supplementing chemotherapy with monoclonal antibodies targeting the HER2 receptor. A second QuanTAV model was trained to predict response to a neoadjuvant regimen combining chemo- and targeted therapy among HER2-positive breast cancer patients. The cohort consisted of 129 patients who were HER2-positive and received treatment with docetaxel, carboplatin, trastuzumab, and/or pertuzumab (TCHP), denoted as the BRCA-TCHP treatment group. Rate of pCR was 51.9%. Survival information was not available for any of the patients in the BRCA-TCHP cohort. 69 patients were divided to the training set ($D_{tr}^2$) and 60 to the testing set ($D_{te}^2$).

As was observed in breast cancer patients receiving BRCA-ACT, poor response to targeted NAC in HER2+ breast cancer was associated with elevated vessel torsion. QuanTAV features distinguishing non-response included skewness of vessel orientations within the XY plane and elevated torsion. A set of 4 QuanTAV features (See Table 9, below) comprising the QuanTAV response score was derived from $D_{tr}^2$, achieving a cross-validated AUC of 0.65. Within $D_{te}^2$, the vessel model predicted pCR with AUC=0.63 (95% CI 0.47-0.76, p=0.041). In a multivariate comparison (See Table 10, below), QuanTAV response score was significant within $D_{tr}^2$ (p=0.023) and the full HER2+ cohort (p=0.035), but not Dr e g alone (p=0.19). Hormone receptor status was also significant, and yielded a testing set AUC of 0.64 (95% CI 0.52-0.75, p=0.017). Combining QuanTAV response score with hormone receptor status increased AUC to 0.70 (95% CI 0.53-0.82, p=0.0036), but this increase was not significant as compared to clinical variables only (p=0.12).

Table 9 shows the top features and corresponding coefficients for the LDA classifier to predict pCR in HER2+ breast cancer patients receiving HER2-targeted neoadjuvant chemotherapy, derived in n=69 training set. Expression of features with positive coefficients contributes to a response prediction, while expression of features with negative coefficients contributes to a prediction of non-response.

TABLE 9

Top Features and Corresponding Coefficients to Predict pCR in HER2+ BRCA with HER2-targeted NAC

| Feature Name | Coefficient |
| --- | --- |
| QuanTAV Spatial Organization - XY - Skewness | −0.52 |
| QuanTAV Spatial Organization - Distance-Elevation - Mean | 0.30 |
| QuanTAV Spatial Organization - Distance-Elevation - Median | 0.48 |
| QuanTAV Morphology - Torsion Histogram - Bin 7 | −0.50 |
| Constant | 0.029 |

Figure 11:
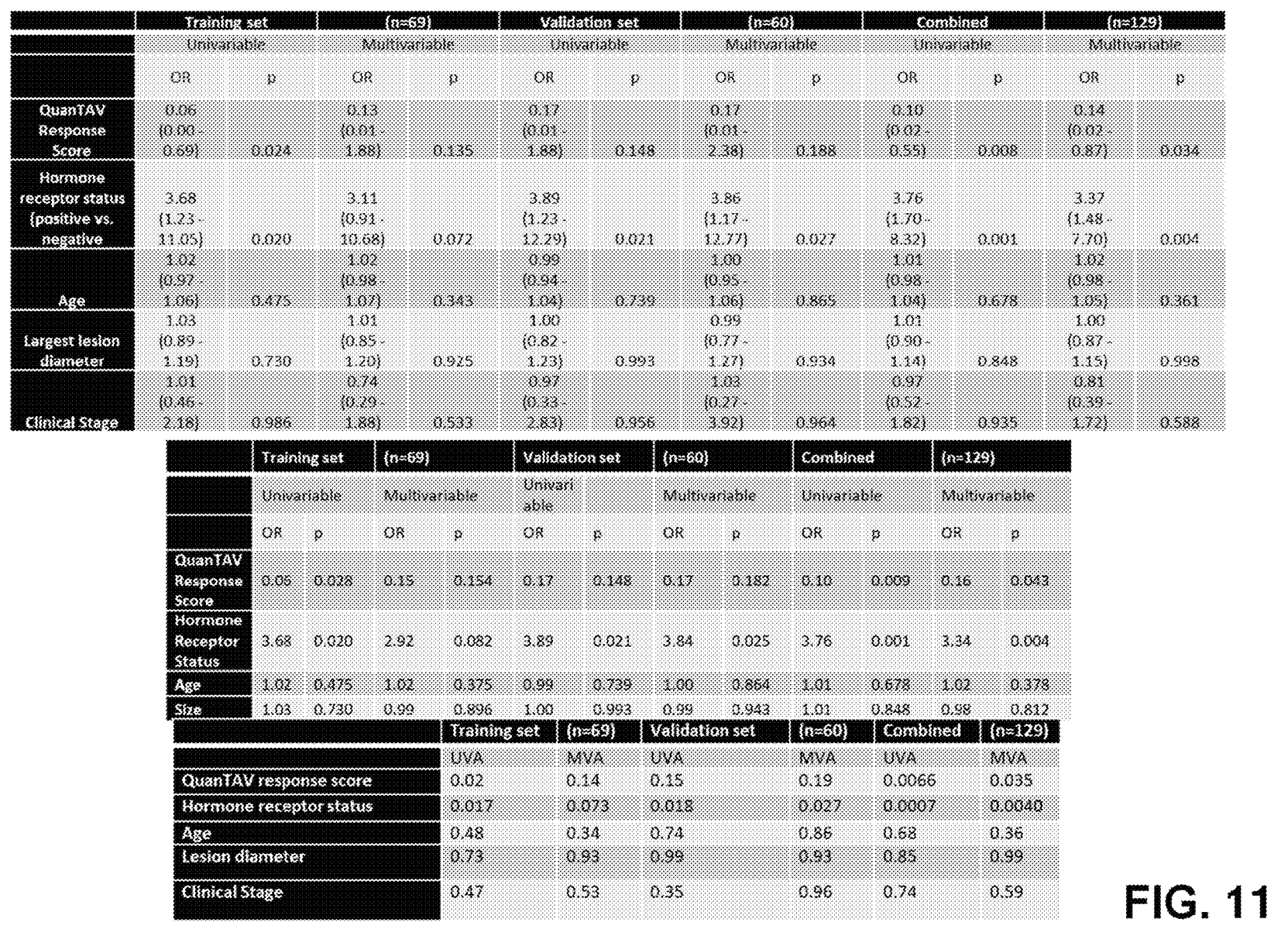

Referring to FIG. 11, illustrated are tables showing univariate (UVA) and multivariable (MVA) analysis of QuanTAV response score and available clinical variables for prediction of pCR to BRCA-TCHP, in connection with various aspects discussed herein. Clinical variables that were individually significant in the training set (hormone receptor status) were incorporated into logistic regression models alone and with QuanTAV response score, and evaluated on the testing set.

Predicting Post-Treatment and Long-Term Progression of NSCLC Following Platinum-Based Chemotherapy (NSCLC-PLAT) from Pre-Treatment CT In advanced NSCLC, platinum-based chemotherapy is standard of care first line treatment for patients lacking actionable mutations. The NSCLC-PLAT cohort consisted of 97 NSCLC patients who received a pemetrexed-based platinum doublet regimen and CT imaging before and after treatment at a single institution. In the absence of surgical samples, response was assessed on post-treatment CT based on change from baseline in longest lesion diameter according to RECIST criteria. 48.0% had responsive or stable disease on post-treatment imaging, and were categorized as responders, while the remaining patients experienced progression. 53 patients were used for training ($D_{tr}^3$) and 44 for testing ($D_{te}^3$).

Figure 12:
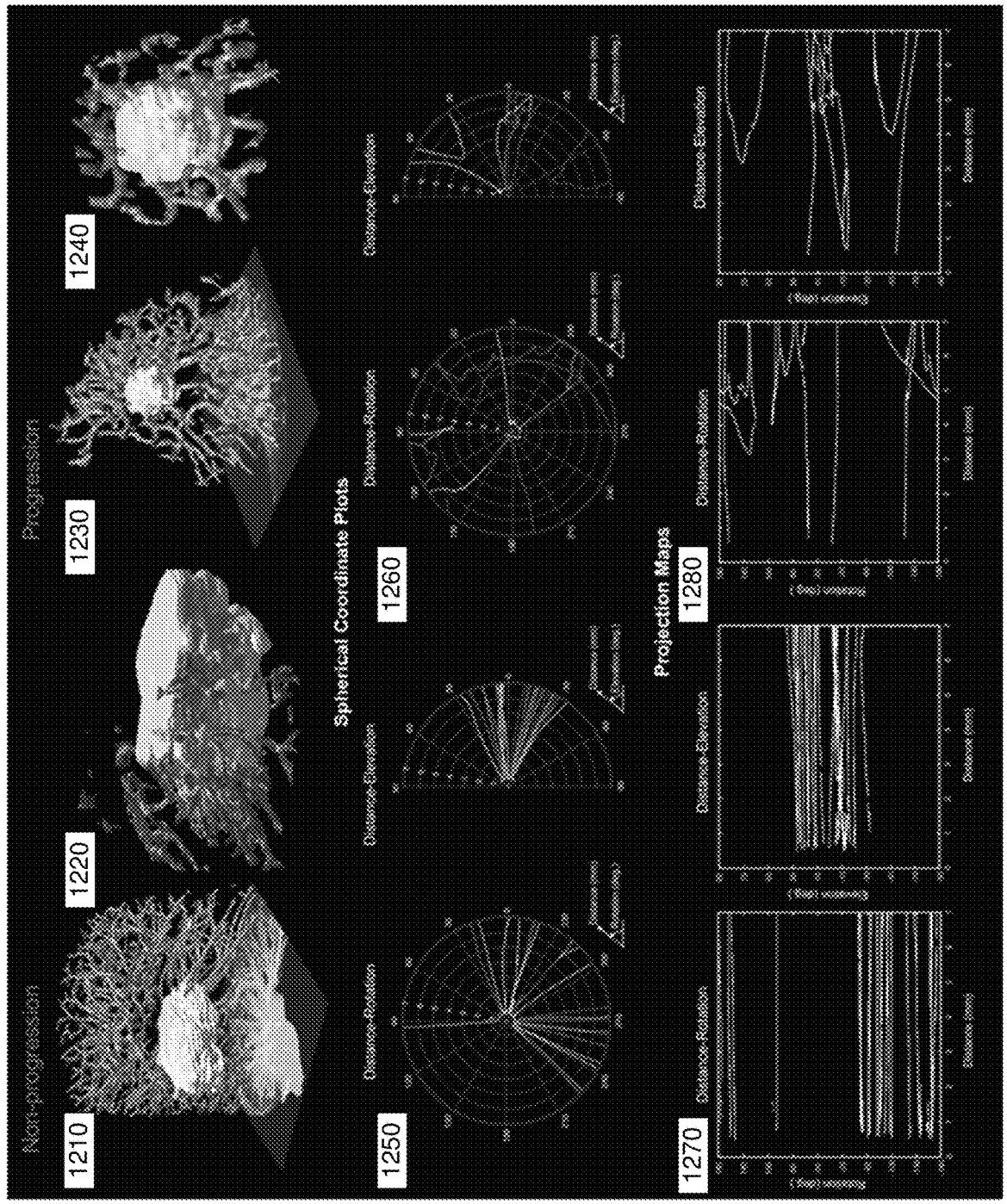
FIG. 12 illustrates example images and graphs showing organization of vascular network at the tumor interface distinguishes NSCLC tumors that experience durable response (left) from those that progress (right) following platinum-based chemotherapy (NSCLC-PLAT), in connection with various aspects discussed herein.

Progression was characterized by TAV organization features corresponding to heterogeneous distribution of vessel orientations, particularly in the region immediately surrounding the tumor. Referring to FIG. 12, illustrated are example images and graphs showing organization of vascular network at the tumor interface distinguishes NSCLC tumors that experience durable response (left) from those that progress (right) following platinum-based chemotherapy (NSCLC-PLAT), in connection with various aspects discussed herein. High vascular density is observed in both non-progressors (1210) and progressors (1230), but differences in the arrangement of tumor-adjacent (1220 and 1240) vessels are detectable through QuanTAV Spatial Organization features. Graphs 1250-1280 show that on projection images depicting rotation around the tumor centroid (left) and elevation above the tumor centroid (right) with respect to distance from the tumor, the standard deviation of vessel orientation was elevated among patients who experienced progression. The position of vessels in a spherical coordinate system relative to the tumor, depicted in polar plots for responders (1250) and non-responders (1260), were used to derive corresponding spherical projection map images (1270 and 1280, respectively). Vessel orientation is computed across projection images locally via a sliding window. Tumors that achieve durable response possessed orderly vasculature with linear paths towards the tumor (1250 and 1270). However, patients who experienced disease progression possessed tumor-adjacent vasculature with twists and deflections from the tumor with respect to distance from its surface (1260), quantifiable as increased standard deviation of orientation on spherical projection images (1280). This abnormal vascular architecture may contribute to poor therapeutic outcome by constraining delivery of chemotherapeutics and promoting a treatment resistant tumor microenvironment.

While many NSCLC tumors shared high vascular density regardless of therapeutic outcome (1210 and 1230), QuanTAV spatial organization features reveal crucial architectural differences between responders (1220) and progressors (1240) at the tumor-vasculature interface. Vessel positions were converted to a spherical coordinate system (1250 and 1260), which were used to derive projection images of vessel organization relative to the tumor (1270 and 1280). For instance, elevated standard deviation of vessel orientations on projection images reflecting rotation and elevation with respect to distance from the tumor were strongly associated with progression (1280). Conversely, vessels surrounding responsive tumors maintained a consistent orientation towards the tumor's surface (1270). A model of 6 vessel features (See Table 10, below), all selected from the pool of QuanTAV organization features, best distinguished response in $D_{tr}^3$ (cross-validated AUC=0.68). When applied to $D_{te}^3$, QuanTAV response scores significantly distinguished response on post-treatment imaging with AUC=0.70 (95% CI 0.54-0.85, p=0.024). Only age (p=0.041) and QuanTAV response score (p=0.014) were significantly associated with response in a univariate setting in $D_{tr}^3$, but age was not predictive in $D_{te}^3$ (AUC=0.41, 95% CI 0.23-0.61, p=0.83). In a multivariable comparison, QuanTAV response score remained independently significant (p<0.05) in all cohorts (See FIG. 13, discussed below).

Table 10 shows the top features and corresponding coefficients for LDA classifier to predict RECIST response in NSCLC patients receiving platinum-based neoadjuvant chemotherapy, derived in n=53 training set. Expression of features with positive coefficients contributes to a response prediction, while expression of features with negative coefficients contributes to a prediction of non-response.

TABLE 10

Top Features and Corresponding Coefficients to Predict RECIST in NSCLC with Platinum-based NAC

| Feature Name | Coefficient |
| --- | --- |
| QuanTAV Spatial Organization - XZ - Kurtosis | 0.86 |
| QuanTAV Spatial Organization - XZ - Skewness | −0.53 |
| QuanTAV Spatial Organization - Distance-Rotation - Skewness | −0.44 |
| QuanTAV Spatial Organization - Distance-Elevation - Standard Deviation | −0.98 |
| QuanTAV Spatial Organization - XZ - Median | −1.02 |
| QuanTAV Spatial Organization - Distance-Rotation - Mean | −0.22 |
| Constant | −0.015 |

Referring to FIG. 13, illustrated are tables showing univariate (UVA) and multivariable (MVA) analysis of QuanTAV response score and available clinical variables for prediction of RECIST response in NSCLC-PLAT recipients, in connection with various aspects discussed herein. Clinical variables that were individually significant in the training set (age) were incorporated into logistic regression models alone and with QuanTAV response score, and evaluated on the testing set.

In the group of patients who received NSCLC-PLAT with survival information available (n=92), a model was trained to estimate progression-free survival (PFS), defined as the period of time following initiation of chemotherapy until progression on imaging, metastasis, or death. Median time to progression was 1 month, and PFS was 27.5% and 8.5% at 1 and 5 years, respectively. Among patients who did not progress (n=17), median follow up time was 36 months. A QuanTAV risk score of 15 features (See Table 11, below) and a corresponding risk group threshold were derived in $D_{tr}^3$ (n=53) (See Table 6, above). Within $D_{te}^3$ (n=39), risk group (p=0.034, HR=2.23, 95% CI 1.07-4.50, C-index=0.62), but not risk score (p=0.14, HR=1.12, 95% CI 0.96-1.31, C-index=0.61), was significantly associated with PFS. In a multivariable Cox proportional hazards (See Table 12, below) including pre-treatment clinical variable (histology, stage, smoking history, sex, and age) and post-treatment outcome information (response on imaging), QuanTAV risk group was the only covariate found to be approaching significance (p=0.071, HR=2.20, 95% CI 0.93-5.20) within the testing set. When compared with pre-treatment information only (i.e. excluding response on imaging), QuanTAV risk group was the only variable to significantly associated with PFS in a multivariable setting (p=0.034, HR=2.39, 95% CI 1.07-5.33).

Table 11 shows the set of features selected by the elastic-net Cox regression model as being most prognostic of PFS on the n=53 patient training set following inception of platinum-based chemotherapy among lung cancer patients and corresponding hazard ratios. The hazard ratios shown here reflect the risk of an increase of one standard deviation in feature value on the training set. A hazard ratio of less than 1 implies that an increase in that feature's value is associated with reduced risk, while a hazard ratio greater than 1 implies the opposite.

TABLE 11

Features Most Prognostic of PFS with HRs After Pt-based NAC for NSCLC

| Feature Name | Hazard Ratio |
| --- | --- |
| Normalized Vessel Volume | 0.48 |
| QuanTAV Morphology - Global Curvature - Kurtosis | 0.61 |

TABLE 11-continued

Features Most Prognostic of PFS with HRs
After Pt-based NAC for NSCLC

| Feature Name | Hazard Ratio |
|---|---|
| QuanTAV Spatial Organization - XZ - Skewness | 0.73 |
| QuanTAV Morphology - Kurtosis of Curvature Per Vessel - Standard Deviation | 0.75 |
| QuanTAV Morphology - Global Curvature - Skewness | 0.86 |
| QuanTAV Morphology - Maximum Curvature per Vessel - Mean | 0.88 |
| QuanTAV Morphology - Skewness of Curvature Per Vessel - Kurtosis | 0.90 |
| QuanTAV Morphology - Skewness of Curvature Per Vessel - Skewness | 0.97 |
| QuanTAV Morphology - Torsion Histogram - Bin 8 | 1.07 |
| QuanTAV Spatial Organization - Distance-Elevation - Mean | 1.16 |
| QuanTAV Spatial Organization - Distance-Rotation - Kurtosis | 1.28 |
| QuanTAV Spatial Organization - Distance-Elevation - Standard Deviation | 1.80 |
| QuanTAV Spatial Organization - Distance-Rotation - Standard Deviation | 2.24 |
| QuanTAV Spatial Organization - XZ - Median | 2.70 |
| QuanTAV Spatial Organization - Distance-Elevation - Kurtosis | 2.86 |

Referring to FIG. 14, illustrated is a table showing Cox proportional hazard univariate (UVA) and multivariable (MVA) analysis of 10-year progression free survival following NSCLC-PLAT treatment, including QuanTAV risk score and available clinical variables, in connection with various aspects discussed herein.

Predicting Response and Recurrence to Trimodality Therapy (NSCLC-TRI) from Pre-Treatment CT For patients with stage III resectable NSCLC, survival can be significantly improved by supplementing platinum-based chemotherapy with radiotherapy and surgical intervention, also known as tri-modality therapy and denoted here as NSCLC-TRI. The NSCLC-TRI cohort was comprised of 90 patients who received pre-treatment CT, followed by neoadjuvant chemoradiation and surgery at a single institution. 41.1% of trimodality recipients achieved major pathologic response (MPR), defined as 10% or less residual viable tumor after neoadjuvant chemoradiation and is the recommended surrogate endpoint in resectable NSCLC. Patients were divided randomly into training (n=46, $D_{tr}^4$) and held-out testing cohorts (n=44, $D_{te}^4$).

A classifier including 4 vessel features (See Table 12, below) was derived within $D_{tr}^4$ (cross-validated AUC=0.71). When evaluated on $D_{te}^4$, QuanTAV response score distinguished MPR with AUC=0.71 (95% CI 0.51-0.84, p=0.0093). QuanTAV response score was significantly associated with MPR in a multivariable comparison within $D_{te}^4$ (p=0.012). Histology (adenocarcinoma vs. squamous cell carcinoma/other), was individually significant (p=0.0075) in $D_{tr}^4$ and predicted MPR with AUC=0.73 (95% CI 0.59-0.86, p=2e-4) in $D_{te}^3$. Combined, QuanTAV response score and histology combination increased AUC to 0.85 (95% CI 0.69-0.94, p=2E-5), a significant improvement over the clinical model (p=0.032).

Table 12 shows the top features and corresponding coefficients for LDA classifier to predict MPR in NSCLC patients receiving neoadjuvant chemoradiation, derived in n=44 training set. Expression of features with positive coefficients contributes to a response prediction, while expression of features with negative coefficients contributes to a prediction of non-response.

TABLE 12

Top Features and Coefficients for Predicting MPR in NSCLC with Neoadjuvant Chemoradiation

| Feature Name | Coefficient |
|---|---|
| QuanTAV Spatial Organization - Distance-Elevation - Kurtosis | −0.89 |
| QuanTAV Morphology - Skewness of Curvature Per Vessel - Kurtosis | 1.21 |
| QuanTAV Spatial Organization - Distance-Rotation - Mean | 0.71 |
| QuanTAV Morphology - Torsion - Max | 0.41 |
| Constant | −0.14 |

Finally, the capability of QuanTAV measures to predict 10-year RFS from date of surgery in recipients of trimodality therapy was assessed. Of the patients who experienced recurrence or metastasis (n=37), median time to event was 1.47 years. Median follow up time among patients without recurrence (n=53) was 3.34 years. A QuanTAV risk score incorporating 15 vessel features (See Table 13, below) and risk groups was derived in $D_{tr}^4$ (n=46) to significantly separate patients by RFS (See Table 6, above). When applied to the held-out testing cohort (n=44), QuanTAV risk score (p=0.039, HR=1.28, 95% CI 1.01-1.62, C-index=0.66) and categorical risk groups (p=0.036, HR=3.66, 95% CI 1.49-8.97, C-index=0.64) were significantly prognostic. We next assessed QuanTAV risk score within the testing cohort for prognostic independence in a multivariable setting (See Table 14, below) including baseline clinical variables (age, sex, histology, clinical stage, chemotherapy regimen, ECOG performance status, and induction dose), as well as features of pathologic (vascular invasion, lymphatic invasion, MPR) and radiologic (RECIST progression vs. response/stable disease) assessment at time of surgery. Of these, only the QuanTAV model (p=0.037) was significant in a comparison with continuous risk score. Categorical QuanTAV risk group was similarly significant in a multivariable setting (p=0.013), along with presence of vascular invasion (p=0.025, HR=12.28, 95% CI 1.36-111) and ECOG performance status (p=0.041, HR=9.22, 95% CI 1.09-77.9). Increases in the standard deviation of curvature of curvature across the length of the vessel was associated with elevated risk of recurrence (See FIG. 9 at 930), whereas tumors who would achieve durable response possessed fewer local variations in curvature due to bends and twists. Similar to the risk score derived for NSCLC patients receiving chemotherapy alone, QuanTAV Spatial Organization features measuring standard deviation of vessel orientation relative to the tumor centroid were associated with recurrence or metastasis following surgery.

Table 13 shows the set of features selected by the elastic-net Cox regression model as being most prognostic of RFS from date of surgery among lung cancer patients receiving trimodality therapy and corresponding hazard ratios, derived within the n=44 patient training set. The hazard ratios shown here reflect the risk of an increase of one standard deviation in feature value on the training set. A hazard ratio of less than 1 implies that an increase in that feature's value is associated with reduced risk, while a hazard ratio greater than 1 implies the opposite.

TABLE 13

Features Most Prognostic of RFS with HRs for NSCLC-TRI

| Feature Name | Hazard Ratio |
|---|---|
| QuanTAV Morphology - Skewness of Curvature Per Vessel - Kurtosis | 0.71 |

TABLE 13-continued

Features Most Prognostic of RFS with HRs for NSCLC-TRI

| Feature Name | Hazard Ratio |
|---|---|
| QuanTAV Spatial Organization - YZ - Skewness | 0.77 |
| QuanTAV Morphology - Torsion Histogram - Bin 9 | 0.82 |
| QuanTAV Spatial Organization - Distance-Rotation - Median | 0.90 |
| QuanTAV Spatial Organization - XY - Standard Deviation | 0.92 |
| QuanTAV Spatial Organization - Rotation-Elevation - Skewness | 0.93 |
| QuanTAV Spatial Organization - YZ - Kurtosis | 0.98 |
| QuanTAV Morphology - Torsion Histogram - Bin 10 | 0.99 |
| QuanTAV Spatial Organization - XY - Mean | 0.99 |
| QuanTAV Morphology - Curvature Histogram - Bin 6 | 1.006 |
| QuanTAV Morphology - Maximum Curvature per Vessel - Mean | 1.050 |
| QuanTAV Spatial Organization - Distance-Rotation - Kurtosis | 1.065 |
| QuanTAV Morphology - Skewness of Curvature Per Vessel - Mean | 1.080 |
| QuanTAV Spatial Organization - Distance-Rotation - Standard Deviation | 1.24 |
| QuanTAV Morphology - Deviation of Curvature Per Vessel - Standard Deviation | 1.31 |

Referring to FIG. 15 illustrated is a table showing Cox proportional hazard univariate (UVA) and multivariable (MVA) analysis of 10-year recurrence free survival following NSCLC-TRI treatment, including QuanTAV risk score and available clinical variables, in connection with various aspects discussed herein.

Discussion

The third example use case presented a novel pan-cancer prognostic and predictive computational imaging biomarker that leverages morphologic measurements of the twistedness and architecture of the tumor-associated vasculature. These vessel-based measurements were found to predict response and survival following intervention across two cancers, two imaging modalities, four chemotherapy-related treatment strategies, and a total of 558 patients. The construction of the tumor's vascular network through neo-angiogenesis plays a crucial role in the determination of patient outcomes by fostering a tumor microenvironment that promotes tumor progression and therapeutic resistance. The structural abnormality of the resultant vasculature directly opposes successful therapeutic intervention, possibly owing to poorer delivery of therapeutic agents to the tumor bed, while also encouraging the formation of hypoxic regions that reduce efficacy of therapeutic agents and accelerate the development of drug resistant subclones. Consistent with the known deleterious role of abnormal tumor vascularization, it was found that the expression of features reflecting erratic vascular shape and arrangement were predictive of poor response and elevated risk following chemotherapeutic intervention. These findings suggest the critical role played by the tumor-associated vessel network across cancer domains in promoting therapeutic response and outcome.

In breast cancer, QuanTAV measurements on pre-treatment dynamic contrast-enhanced MRI predicted patient outcomes following neoadjuvant treatment with two standard-of-care therapeutic strategies in need of validated predictive markers. First, a chemotherapy-only regimen of BRCA-ACT, standard first line neoadjuvant treatment for the majority of breast cancer patients whose tumors are clinically HER2-negative, there exists no targeted neoadjuvant treatment options. Accordingly, they will receive a standardized chemotherapy-only regimen of BRCA-ACT prior to surgery, to which only roughly a quarter will achieve a pathological complete response. The third example use case demonstrated that machine learning models of QuanTAV features could predict pathologic response and 10-year RFS independent of response-associated receptor subtype. Second, while the addition of therapies targeting the HER2-receptor to neo-adjuvant chemotherapy has substantially improved outcomes for clinically HER2-positive patients, a significant portion of these tumors still ultimately fail to achieve full pathologic response respond to a targeted BRCA-TCHP regimen. The ability of QuanTAV to predict pathologic response to HER2-targeted therapy is consistent with the role of the HER2 receptor in promoting tumor angiogenesis.

These findings were mirrored in advanced NSCLC, where QuanTAV measures extracted from pre-treatment CT volumes were associated with both response and survival following two intervention strategies. First, for advanced NSCLC patients without actionable mutation, a platinum-based chemotherapy regimen is standard first-line intervention (NSCLC-PLAT). However, only 24%-31% of patients will achieve response and there are no clinically validated biomarkers for the guidance of platinum-based chemotherapy by benefit. QuanTAV measures were associated with response on post-treatment imaging according to RECIST criteria, as well as progression-free survival. Second, for patients with stage III resectable NSCLC, survival can be significantly improved by a trimodality regimen supplementing platinum-based chemotherapy with radiotherapy and surgical intervention. However, trimodality therapy lacks predictive pre-treatment markers of benefit and bears a high rate of mortality between 5% and 15%. Elevated disorganization and twistedness of the TAV on imaging was associated with a failure to achieve pathologic response and poorer 10-year recurrence-free survival. These findings are in agreement with the crucial role of the TAV in NSCLC outcomes, evidenced by the importance of lymphovascular invasion as a prognostic marker and the benefits of TAV-normalization via anti-angiogenic therapy for many NSCLC patients.

Critically, measurements of the third example use case offered prognostic value independent of measures of functional volume on DCE-MRI (See Tables 7 and 8, above), suggesting limitations of perfusion imaging's ability to fully characterize the TAV. Morphologic aberrations of the TAV on radiology have previously been shown to be elevated in the case of breast and NSCLC malignancy, as compared to benign lesions. Reduction in the tortuosity of the TAV on high-resolution brain MR angiography throughout treatment has been shown to be associated with favorable treatment outcome in metastatic breast cancer. Conversely, un-normalized vessel tortuosity following treatment provide an earlier indication of treatment failure than monitoring tumor growth. The third example use case is the first study to date demonstrating the potential of 3D vascular morphology for predicting therapeutic outcomes prior to treatment, as well as the most comprehensive investigation of its role as a predictive and prognostic biomarker across cancers and imaging modalities.

QuanTAV analysis represents a new addition to an expanding body of work on the potential of quantitative imaging features mined from radiology to serve as predictive biomarkers: an approach known as radiomics. One of the most frequently deployed families of radiomic features is image texture, which quantify the heterogeneity or spatial arrangement of image signals. Across numerous cancers and imaging modalities, texture-based biomarkers of the tumor and its environment have allowed for stratification of tumors into clinically significant biology- and outcome-associated groups. In breast cancer, textural patterns of the tumor, peri-tumoral surroundings, bulk parenchyma, and lymph nodes on imaging has shown associations with risk and responsiveness to neoadjuvant therapy. Likewise, in NSCLC, textural analysis of the tumor and peri-tumoral lung parenchyma has shown promise in predicting benefit of a number of therapeutic approaches, including chemoradiation with and without surgery, targeted therapy, and immunotherapy. Consistent across both cancers, evidence suggests that elevated textural heterogeneity portends poor prognosis and increased risk of non-response. Tortuous tumor vasculature plays an established role in fostering a heterogeneous, treatment resistant tumor microenvironment. Thus, a disorganized TAV may facilitate the creation a texturally complex tumor microenvironment that forms the basis of a significant portion of prognostic radiomic signatures. This hypothesis is supported by previous work noting that prognostic textural radiomic patterns of heterogeneity within the peri-tumoral regions of NSCLC are also associated in part with molecular pathways regulating angiogenesis. To investigate a potential explanatory role between the TAV and prognostic texture signatures, QuanTAV features and risk score were compared with a previously published intra- and peri-tumoral texture-based risk score derived within the NSCLC-TRI cohort (See Table 14, below). Vessel and texture-based risk scores were found to be significantly correlated (p=0.23, p=0.030). Of the five most prognostic individual QuanTAV features, reduced variability of curvature along vessels was inversely correlated with texture-derived risk score (p=−0.41, p=0.0001). The findings warrant additional study of the potential role of angiogenesis as a basis for image texture-based biomarkers.

Table 14 shows correlation of the top 5 most prognostic QuanTAV features and QuanTAV risk score with risk score derived from intra- and peri-tumoral texture features within the NSCLC-TRI cohort.

TABLE 14

Correlation and p-value of Top 5 Features for NSCLC-TRI

| Feature | Correlation Coefficient | p-value |
| --- | --- | --- |
| QuanTAV Morphology - Torsion Histogram - Bin 9 | 0.070 | 0.51 |
| QuanTAV Spatial Organization - Distance-Rotation - Standard Deviation | −0.053 | 0.63 |
| QuanTAV Spatial Organization - YZ - Skewness | −0.044 | 0.68 |
| QuanTAV Morphology - Deviation of Curvature Per Vessel - Standard Deviation | 0.0159 | 0.88 |
| QuanTAV Morphology - Skewness of Curvature Per Vessel - Kurtosis | −0.408 | 6.5E−05 |
| QuanTAV Prognostic Risk Score | 0.229 | 0.030 |

The findings suggest that patients with convoluted vasculature at time of treatment are less likely to derive benefit from systemic therapeutic intervention. Resultantly, patients flagged as non-responders based upon analysis of the TAV may benefit from anti-angiogenic therapy. In NSCLC, bevacizumab, an anti-antiangiogenic targeted therapy, in combination with chemotherapy provides therapeutic benefit by blocking the VEGF receptor, down-regulating tumor angiogenesis, and facilitating delivery of other systemic therapeutics. However, bevacizumab is currently prescribed conservatively in NSCLC due to its toxicity and current lack of validated predictive markers of therapeutic benefit. QuanTAV measurements could potentially identify NSCLC patients who would benefit from vascular normalization through the addition of anti-VEGF therapy to their therapeutic regimen. The role of bevacizumab in breast cancer remains controversial, having been previously approved and subsequently revoked for treatment of metastatic breast cancer by the FDA due to safety concerns. However, its use in the neoadjuvant setting in combination with chemotherapy has been shown to improve rate of pathologic response and overall survival in breast cancer subsets with specific receptor status and genotype. These results illustrate the important role of patient selection in success of vascular normalization and raise the question of whether anti-angiogenic therapies could still be an effective therapeutic option given more effective tools for targeting their application. Future work should explore the potential association of QuanTAV phenotype and benefit of anti-angiogenic therapy in NSCLC and breast cancer.

The third example use case had some limitations that can be improved on in various embodiments. First, the segmentation protocol was formulated to achieve a balance of accuracy and efficiency in order to enable analysis within such a large cohort. To assess the robustness of our approach, the performance of TAV-based response scores in a breast MRI and lung CT dataset was evaluated following various levels of perturbation to vessel masks through morphological image processing operations at branch and endpoints. Encouragingly, QuanTAV signatures were found robust to noise in vessel segmentations, with no significant changes to QuanTAV response score AUC at any level of perturbation observed (See FIG. 16, discussed below). Beyond this experiment, it is encouraging that even accounting for segmentation errors, the approach was found to be predictive and prognostic in a wide number of use cases. However, various embodiments or future work exploring more sophisticated methods of isolating the tumor vasculature, such as specialized deep learning segmentation strategies, can further improve the strength of TAV analysis. Second, breast MRI datasets were assembled across institutions and trials, and, resultantly, imaging data was highly heterogeneous in acquisition protocol, a confounder we attempted to minimize through preprocessing strategies. Encouragingly, unsupervised clusterings of top QuanTAV features via UMAP did not reveal site-based batch effects in either breast cancer cohort (See FIG. 17, discussed below). Third, across the datasets analyzed, different clinical endpoints were utilized for response (pCR, MPR, and RECIST response) and survival (RFS and PFS), due to differing accepted and feasible clinical endpoints in the various clinical contexts. Most significantly, patients in the platinum-based chemotherapy cohort did not receive surgery, and thus response could only be assessed on post-treatment imaging according to RECIST criteria, rather than by pathologist assessment of surgical specimens. Finally, further validation of the approach is required in a prospective setting prior to clinical adoption. QuanTAV-based biomarkers should next be evaluated for their ability to predict well-defined clinical endpoints such as pathologic response among patients enrolled in clinical trials including chemotherapy.

Referring to FIG. 16, illustrated are example images and a bar graph evaluating the robustness of QuanTAV-based response prediction to errors in vessel segmentation within a breast MRI (BRCA-ACT, n=141) and lung CT (NSCLC- TRI, n=46) testing set, in connection with various aspects discussed herein. At the top of FIG. 16, example images show vessel segmentations that were randomly eroded and dilated at branchpoints and endpoints for increasing numbers of iterations. Vessel voxels in red were retained in the vasculature following perturbation, blue voxels indicate portions of the vasculature removed by perturbation. At the bottom of FIG. 16, a graph shows QuanTAV response scores that were re-computed using the vessel network at various levels of perturbation. Robustness of QuanTAV response score was assessed by computing the AUC of the ROC curves at each perturbation level (5, 10, 15, and 20 iterations of perturbation). When compared with the ROC curve of the QuanTAV response score computed with the original skeletons via Delong's test, no level of perturbation was found to produce a significant difference in AUC in either the NSCLC-TRI ($p=0.12$-$0.65$) or BRCA-ACT ($p=0.11$-$0.30$) cohorts.

Figure 17:
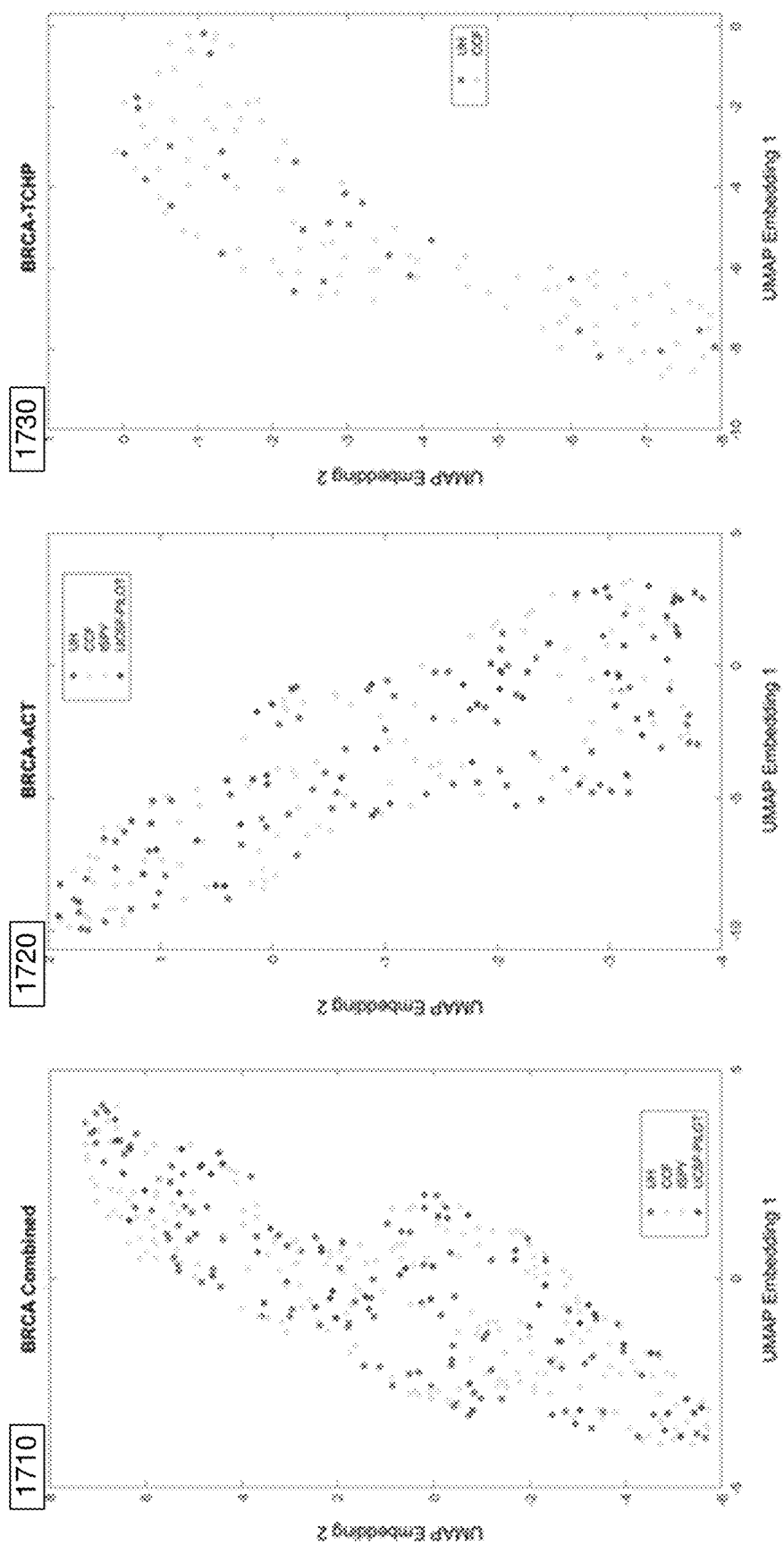
FIG. 17 illustrates UMAP projections of QuanTAV features for all breast cancer patients (1710), the HER2-negative cohort receiving BRCA-ACT (1720), and the HER2-positive cohort receiving BRCA-TCHP (1730), shaded according to site, in connection with various aspects discussed herein.

Referring to FIG. 17, illustrated are UMAP projections of QuanTAV features for all breast cancer patients (1710), the HER2-negative cohort receiving BRCA-ACT (1720), and the HER2-positive cohort receiving BRCA-TCHP (1730), shaded according to site, in connection with various aspects discussed herein. Some separation by site is observed across all patients (1710), but this effect disappears when separated by HER2 status/treatment cohort (1720 and 1730). In FIG. 17, UH: University Hospitals, CCF: Cleveland Clinic Foundation, ISPY: ISPY1-TRIAL, UCSF-PILOT: University of California San Francisco ISPY1 pilot study.

Methods

Breast Datasets. A total of 470 patients who received breast neoadjuvant chemotherapy with pre-treatment dynamic contrast-enhanced (DCE) MRI were identified for this study. 31 patients were excluded due to poor image quality resulting in flawed vascular segmentation (including low spatial resolution, insufficient temporal scans or poor temporal resolution, severe artifacts, or inadequate vessel enhancement). 68 patients were HER2-positive, but received treatment prior to the introduction of anti-HER2 agents, and were thus excluded from analysis. The total number of patients for analysis was 371. 115 achieved pathological complete response (pCR), defined as the absence of any residual invasive tumor in the tumor bed or axilla following NAC. Patients received different NAC regimens based on the expression of the HER2 receptor, and patients were split into corresponding treatment groups for analysis.

BRCA-ACT: 242 patients were HER2-negative, and received an anthracycline-based regimen with or without a taxane. Following NAC, 48 patients achieved pCR and 194 retained the presence of residual disease (non-pCR). This cohort included patients from the ISPY1 (n=109) and Breast-NAC Pilot (n=48) studies that also had recurrence-free survival (RFS) information available. Within this subset, assessed 10-year RFS from the initiation of NAC (RFS for the Breast-NAC MRI Pilot study was recorded following completion of NAC, but was adjusted based on the duration of NAC according to the study protocol). 48 patients experienced recurrence, with a median time to recurrence of 77.7 months.

BRCA-TCHP: A multi-institutional cohort of 129 HER2+ patients who received targeted NAC at institution 1 (n=28) or institution 2 (n=101) was also assessed. The majority of patients received NAC supplemented with trastuzumab and pertuzumab (n=125), while five patients from institution 1 received only trastuzumab. 67 patients achieved pCR and 62 non-pCR. No BRCA-TCHP patients had survival information available.

Lung Datasets. A total of 192 standard dose, non-contrast lung CT volumes collected prior to treatment were included for analysis. Patients were treated and imaged at Institution 1, and were divided into two groups depending on the type of therapeutic regimen that they received (i.e. trimodality or pemetrexed chemotherapy).

NSCLC-PLAT: A total of 97 patients who received platinum-based chemotherapy without surgical intervention at Institution 2 with available pre-treatment CT scans were identified. In the absence of post-treatment surgical samples, response was determined by RECIST criteria based on size changes between pre- and post-treatment CT. 47 patients were identified as responders, indicated by response or stable disease following platinum-based chemotherapy, while 49 had progression on imaging and were deemed non-responders. 92 patients had progression-free survival (PFS) information available, which was defined as the time from initiation of treatment to the detection of progressive disease or death, whichever occurred earlier, and was censored at the date of last follow-up for those alive without progression.

NSCLC-TRI: 90 patients received trimodality therapy, consisting of neoadjuvant chemoradiation followed by surgical intervention. Response was assessed by major pathologic response (MPR), defined as $\leq 10\%$, residual tumor noted on resected specimens and the suggested clinical endpoint for neoadjuvant treatment in resectable non-small cell lung cancer. 36 patients achieved MPR. Disease free survival (DFS) was measured from the date of surgery to the date of recurrence or the date of death, whichever occurred earlier, and censored at the date of last follow-up for those alive without disease recurrence.

Dataset stratification. For each treatment group, patients were divided into training and testing sets. Models were developed and optimized on the training set, then applied to the testing set. Three of the treatment groups (BRCA-TCHP, NSCLC-PLAT, NSCLC-TRI) had response rates of approximately 50%, and were accordingly divided randomly in half for training and testing, when possible using the same splits from prior studies. Relative to these treatment strategies, the rate of response to BRCA-ACT is substantially lower. Given the potential of training data imbalanced between categories to negatively impact classifier performance and robustness, a BRCA-ACT training cohort was randomly chosen containing 50% of responders and enough non-responders to enforce a 3:1 class balance (previously shown to limit the negative effects of class imbalance for an LDA classifier). The composition of each training and testing set is summarized in Table 15, below.

Table 15 shows the composition of training and testing sets for each treatment cohort, including number of patients with available post-treatment response and survival information. pCR, pathologic complete response, MPR, major pathologic response, RECIST, Response Evaluation Criteria In Solid Tumors, RFS, recurrence-free survival, PFS, progression-free survival.

TABLE 15

Compositions of Training and Testing sets for Treatment Cohort

| | Training | | | | Testing | | | |
| --- | --- | --- | --- | --- | --- | --- | --- | --- |
| | Response | | Prognosis | | Response | | Prognosis | |
| Cohort | n | Endpoint | n | Endpoint | n | Endpoint | n | Endpoint |
| BRCA-ACT | 98 | pCR | 63 | RFS | 144 | pCR | 93 | RFS |
| BRCA-TCHP | 69 | pCR | 0 | — | 60 | pCR | 0 | — |
| NSCLC-PLAT | 53 | RECIST response | 53 | PFS | 44 | RECIST response | 39 | PFS |
| NSCLC-TRI | 44 | MPR | 44 | RFS | 46 | MPR | 46 | RFS |

Pre-Processing and Segmentation—Lung CT. Each CT image was masked to the lungs only, which were identified by thresholding a range of common attenuation values for lung tissue followed by morphological processing. To ensure consistency in feature computation, all CT volumes were next resized to an isotropic resolution of 1 mm$^3$. Two types of tissue were extracted from CT images from pre-processed images for quantitative analysis: the tumor region itself and the tumor-associated vasculature. Tumor boundaries were manually annotated in 3D across the tumor volume. The tumor-associated vasculature was extracted in several steps. A multi-scale vesselness filter, previously shown to effectively segment pulmonary vasculature on non-contrast CT, was utilized to emphasize tubular vessel-like structures. Next, the filtered volume was divided automatically into multiple regions corresponding to the magnitude of the vesselness filter response, according to thresholds computed by Otsu's method. The region with the highest vesselness filter response (and thus, containing pixels most likely to belong to vessel-like objects) was isolated as the vessel region. The vessel segmentation was further refined by applying a series of morphological operations to remove noise and repair discontinuities, as well as thresholding by original attenuation values to remove remaining non-vessel artifacts. Finally, a fast marching algorithm was applied to the 3D segmented vasculature to identify the center lines of vessels and divide the vessel network into discrete branches.

Pre-Processing and Segmentation—Breast MRI. Unlike CT images, MRI lacks true quantitative values. Accordingly, a preprocessing and segmentation pipeline was employed with more rounds of manual quality control and adjustment (blinded to patient outcome) for MRI data. To isolate vascularized tissue on breast MRI, subtraction volumes depicting the regions of enhancement following administration of contrast agent were derived. The first MRI scan acquired following contrast agent injection was spatially aligned to the pre-contrast scan via affine registration. The difference in image intensities between registered pre- and post-contrast acquisitions was then computed. Intensity values were normalized according to the mean and standard deviation of intensity on the pre-contrast scan. As in CT, subtraction images were resized to an isotropic resolution of 1 mm$^3$. 3D tumor boundaries were obtained with a combination of manual annotation and automated segmentation techniques. On each scan, tumor boundaries were first partially annotated on multiple adjacent 2D slices by an experienced reader. This manually annotated region was supplied as input to a 3-dimensional active contour segmentation algorithm, which expanded the 2D annotated region to a full volumetric tumor segmentation. To segment the tumor vasculature, vesselness filtering was again applied to enhance vessel-like objects within the volume. The resulting filtered volume was segmented at 20 different thresholds using Otsu's method, then refined by morphological operations. The various vessel segmentation thresholds were then assessed for alignment with vessel enhancement in 2D (on maximum intensity projections of subtraction images) and 3D (on subtraction image volumes using 3D slicer software). The threshold that best captured the vasculature for each scan was selected manually by a single reader blinded to clinical data and therapeutic outcome. Finally, center line coordinates and branches of the final vessel network were computed by fast marching.

Measures of QuanTAV Morphology: From 3D vessel skeletons, a set of 61 quantitative vessel tortuosity features, expanded from a set of 35 introduced previously, were computed. The full set of QuanTAV Morphology features is described in Table 2. At each point within a branch, curvature was computed as the inverse of the radius of the circle containing that point and the two adjacent points within the branch. Distribution of curvature was summarized along the entire vasculature and each branch through first order statistics (mean, standard deviation, max, skewness, and kurtosis), and branch-level statistics were summarized at the patient level with the same statistics. For each branch, torsion was computed as one minus the ratio of the Euclidean distance between the first and last points of a branch to the branch's length and summarized at the patient level via first order statistics. The distributions of curvature and torsion across the full vasculature were further summarized via 10-bin histograms. Additional vessel metrics—including vessel volume, length, number of vessels entering the tumor, and percentage of vessels in the vessel network feeding the tumor—were also computed.

Measures of QuanTAV Spatial Organization: A set of 30 features describing the organization of the tumor-associated vasculature, previously described, were computed. The steps for extracting QuanTAV Spatial Organization features are depicted in FIG. 7. From the 3-dimensional map of vessel centerlines, a set of 2D vessel projection images are generated, across which statistics summarizing the local orientation of vessels are computed. Along a projection image, the five most prominent vessel orientations are computed within a local region via Hough transform, a mathematical operation for the detection of lines within an image. The window of analysis is slid along the image to obtain a distribution of vessel orientations across the entire vessel image. The overall distribution of vessel orientations is then summarized by five first order statistics (mean, median, standard deviation, skewness, and kurtosis), which constitute the set of QuanTAV Spatial Organization features.

Vessel network organization is assessed across six projection images. A set of three Cartesian projections is obtained by flattening the vasculature along one of the three spatial dimensions, in the axial, sagittal, or coronal planes. In addition to analyzing the TAV in the original coordinate system, the 3D vasculature can also be converted to a spherical coordinate system in order to capture vessel position relative to the tumor itself. Each vessel point is converted to a spherical coordinate system. Rather than (X, Y, Z) position, spherical coordinates correspond to elevation from the tumor center, rotation about the tumor center, and distance from the tumor surface. As with Cartesian views, the tumor vasculature is projected along each of these dimensions to obtain three 2D projection images: elevation with respect to rotation, rotation with respect to distance, and elevation with respect to distance. Vascular network organization features are computed with two tunable parameters: maximum vessel distance from the tumor to include and size of the sliding window used to compute vessel orientations. These parameters were optimized within each imaging modality/cancer domain.

QuanTAV Predictive Response score. The set of top features that best predicted therapeutic response for each use case in two rounds of Wilcoxon feature selection in cross-validation within the training set was identified. The size of this feature set was determined per cohort based on performance within the training set in cross-validation (see supplement for implementation details). For each cohort, top vessel features were incorporated into a linear discriminant analysis (LDA) classifier and trained across the full training cohort to predict response in the testing set. The output of this classifier was a score between 0 and 1, in turn corresponding to the level of confidence that a patient would achieve a response following the conclusion of therapy.

QuanTAV Prognostic risk score and Groups. For each cohort with survival information available, a survival model was derived in the training set to generate QuanTAV risk scores using a strategy discussed below. Features that were highly correlated and likely redundant were pruned from the feature set, retaining the feature with the highest absolute coefficient value in a multivariate proportional hazards model. A Cox regression model was trained using the remaining vessel features via 10-fold elastic net regularization. The coefficient values for the model were then applied to training and testing sets to derive patient risk scores. A risk score threshold to optimally stratify patients into high and low risk groups was additionally derived in the training set for each cohort.

Association with texture-based risk assessment. Within the NSCLC-TRI cohort, a previously published prognostic risk score for trimodality recipients composed of image texture features was assessed for correlations with prognostic QuanTAV features and risk score. The textural risk score consisted of 2 intra-tumoral features and 3 peri-tumoral features extracted within a 15 mm radius from the tumor. The top five most prognostic features of the QuanTAV signature were assessed for correlation with textural risk score in the full NSCLC-TRI cohort. The correlation with overall QuanTAV prognostic risk score was also assessed.

Effect of Segmentation Error. To investigate the robustness of TAV-based outcome predictions to errors in vessel segmentations, we evaluated the performance of TAV-based response score at various reduced qualities of vessel segmentation. For each iteration, the set of all branchpoints and endpoints within the vessel skeleton were first identified. For each of these points, the vasculature was randomly perturbed with an equal chance to 1) erode the vessel locally, 2) dilate the vessel locally, or 3) make no change. Degraded vessel segmentations were saved after 5, 10, 15, and 20 iterations of perturbations (e.g., see FIG. 16 top, showing an original image, along with 10 and 20 iterations). Skeletons and QuanTAV features were then re-computed for each perturbed segmentation. The experiment was conducted on the testing sets from one breast (BRCA-ACT) and one lung (NSCLC-TRI) treatment group. QuanTAV response scores were then re-derived on the perturbed testing data and AUC was computed, which was then compared against perform of the original model.

Statistical Analysis. The primary metric used to evaluate response prediction models was area under the receiver operating-characteristic curve (AUC). Significance level and 95% confidence intervals of the AUC were computed via permutation testing with Monte Carlo sampling across 50,000 iterations. The univariate association of QuanTAV response score and continuous clinical variables with response was assessed by two-sided Wilcoxon rank sum test. The univariate significance of categorical clinical variables was assessed by chi-squared test. Multivariate significance of classifier output and clinical variables was assessed by chi-squared test of model coefficients. Clinical variables with univariate significance were incorporated into a clinical only logistic regression model, as well as a logistic regression model combining clinical variables with QuanTAV response score. Comparison of paired ROC curves to evaluate the significance of differences in their AUC was performed by Delong's test of correlated ROC curves.

For prognostic models, both the QuanTAV risk score and categorical QuanTAV risk groups were assessed in uni- and multi-variate settings, along with clinical variables, including pathological and treatment response information available at the completion of chemotherapeutic regimen. Univariate association with survival was evaluated for significance by log rank test. Multivariate significance was assessed by chi-squared test of Cox proportional hazards model coefficients. The primary metrics used to evaluate association with survival were hazard ratio (HR) and concordance index (C-index).

Figure 18:
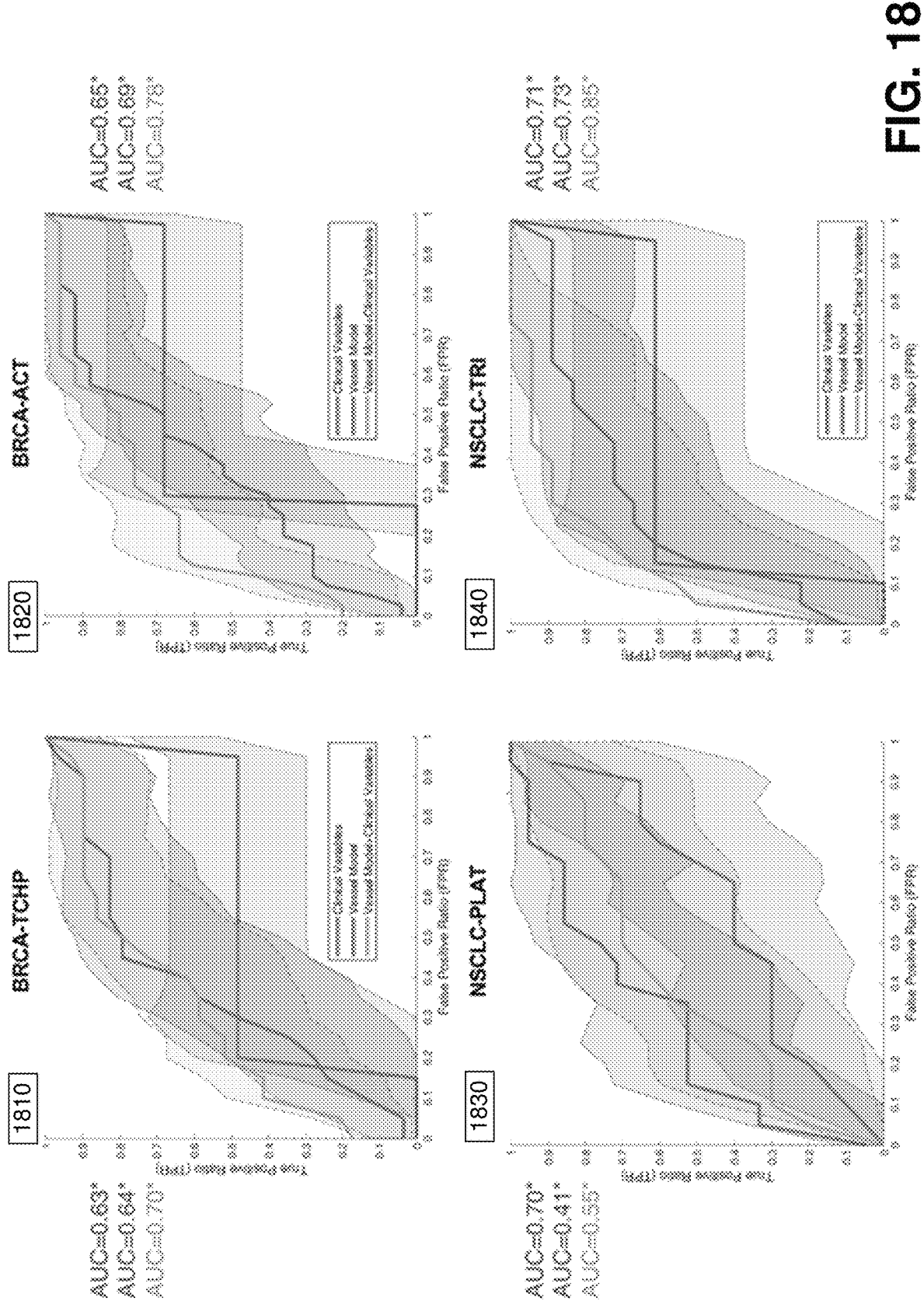
FIG. 18 illustrates four graphs showing receiver operating characteristic (ROC) curves for the QuanTAV response score (blue), clinical model (red), and combined QuanTAV and clinical model (green) in testing sets for the four treatment cohorts, in connection with various aspects discussed herein.
Figure 19:
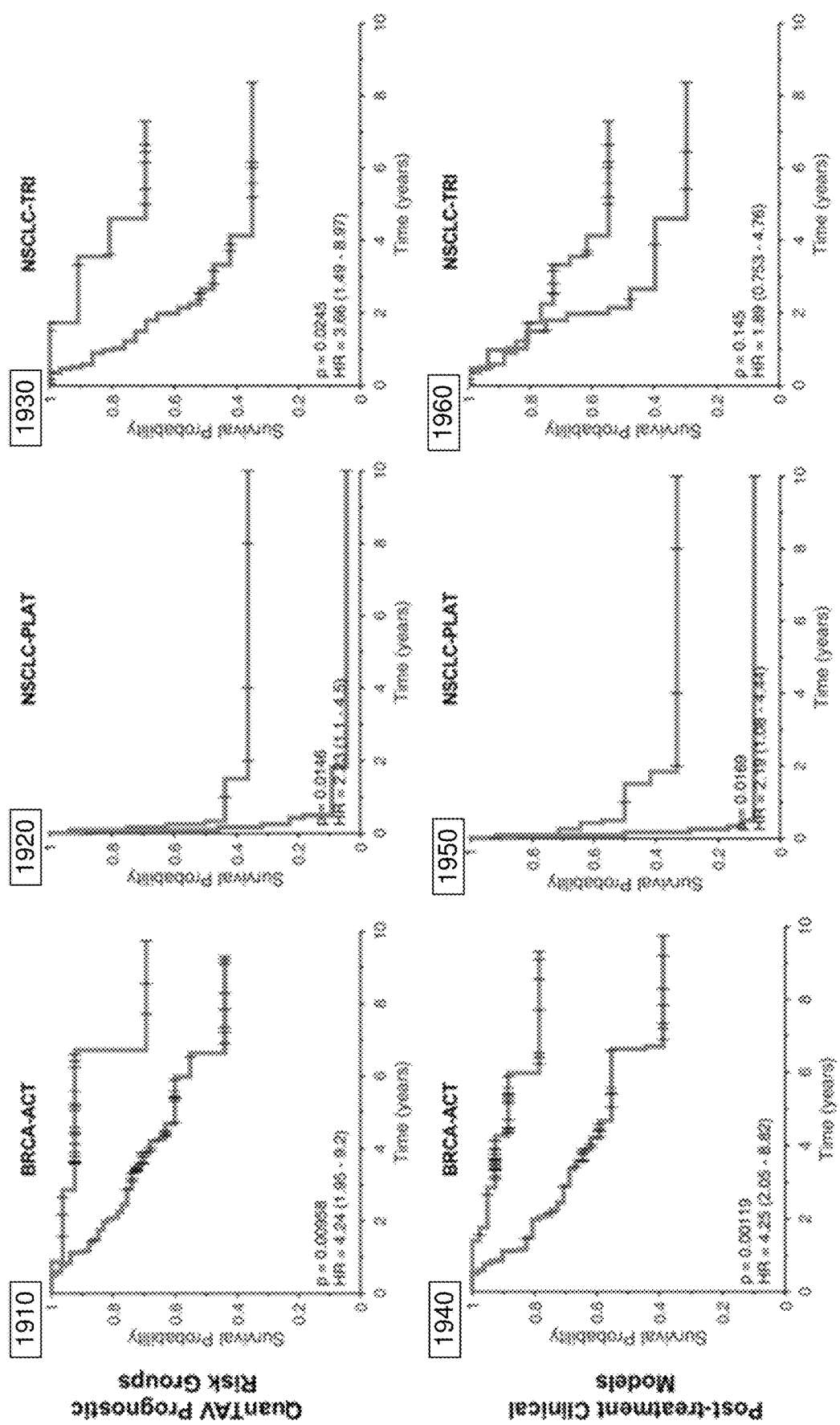
FIG. 19 illustrates six graphs showing Kaplan Meier curves comparing association of risk groups corresponding to pre-treatment QuanTAV risk score and post-treatment clinical model among testing set patients with available survival data, in connection with various aspects discussed herein.
Figure 20:
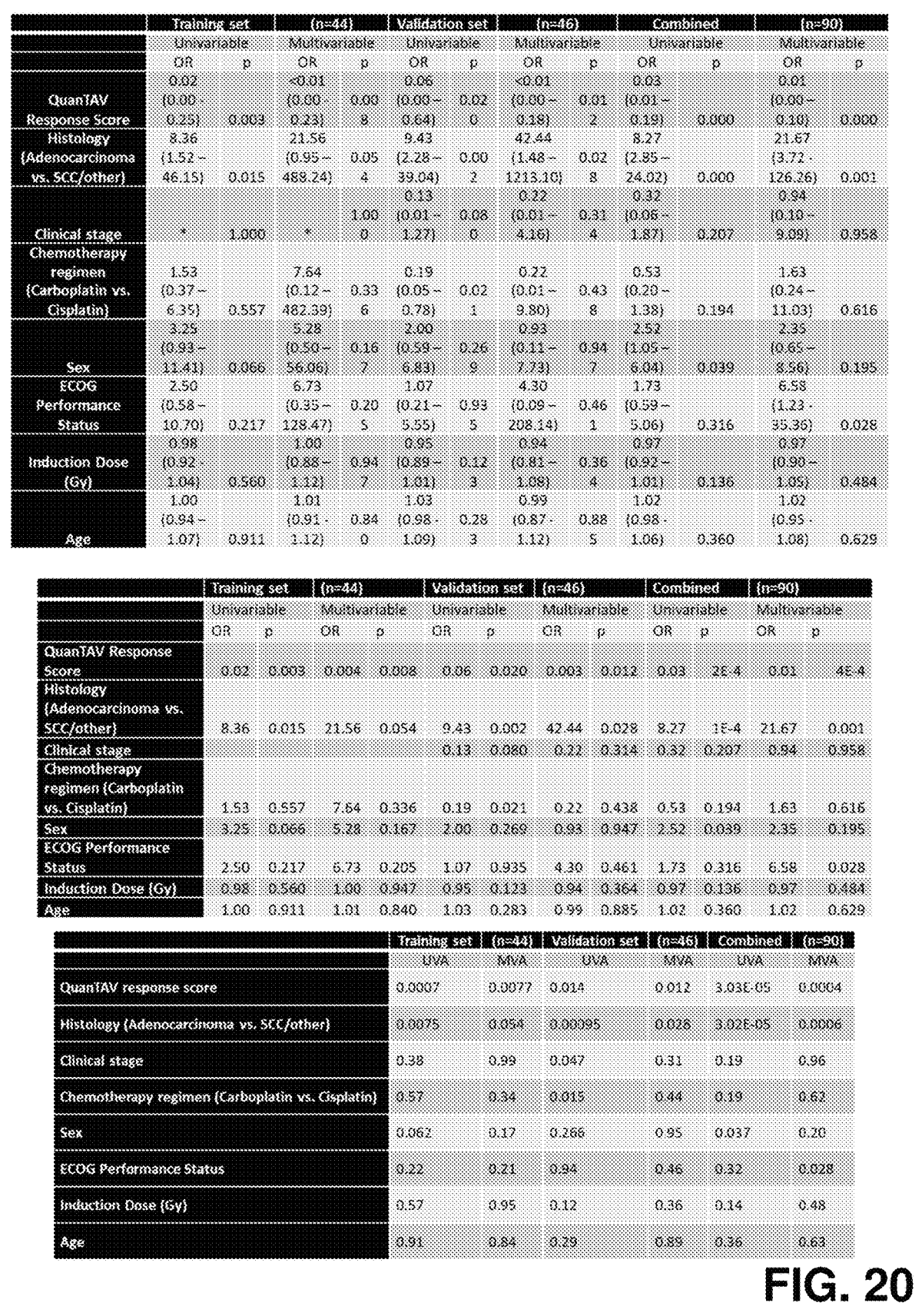

FIGS. 18-20 illustrate additional aspects in connection with the third example use case.

Referring to FIG. 18, illustrated are four graphs showing receiver operating characteristic (ROC) curves for the QuanTAV response score (blue), clinical model (red), and combined QuanTAV and clinical model (green) in testing sets for the four treatment cohorts, in connection with various aspects discussed herein. Graph 1810 shows prediction of pathological response for breast cancer patients receiving HER2-targeted neoadjuvant chemotherapy (BRCA-TCHP, n=69). Graph 1820 shows prediction of pathological response for breast cancer patients receiving anthracycline-based neoadjuvant chemotherapy (BRCA-ACT, n=144). Graph 1830 shows prediction of response on post-treatment imaging for NSCLC patients receiving platinum-based chemotherapy (NSCLC-PLAT, n=44). Graph 1840 shows prediction of pathologic response for NSCLC patients receiving a trimodality regimen of chemoradiation followed by surgery (NSCLC-TRI, n=44).

Referring to FIG. 19, illustrated are six graphs showing Kaplan Meier curves comparing association of risk groups corresponding to pre-treatment QuanTAV risk score and post-treatment clinical model among testing set patients with available survival data, in connection with various aspects discussed herein. QuanTAV risk groups (top) performed comparably to or out-performed clinical models (bottom) incorporating post-treatment response and/or post-surgical pathologic findings with baseline clinicopathologic variables. Top: association of QuanTAV risk groups with 10-year recurrence-free survival following BRCA-ACT (n=93) (at 1910), 10-year progression-free survival following NSCLC-PLAT (n=39) (at 1920), and 10-year recurrence-free survival following NSCLC-TRI (n=46) (at 1930). Bottom: association of clinical models with survival incorporating baseline clinical variables, and response information available at conclusion of treatment. 1940 shows the BRCA-ACT model incorporating baseline clinical variables and pathologic complete response status on surgical sample. 1950 shows the NSCLC-PLAT model incorporating baseline clinical variables and response on post-treatment imaging. 1960 shows the NSCLC-TRI models incorporating baseline clinical variables and major pathologic response status, presence of vascular invasion, presence of lymphatic invasion, and response on post-treatment imaging at time of surgery.

Referring to FIG. 20, illustrated are tables showing univariate (UVA) and multivariable (MVA) analysis of QuanTAV response score and available clinical variables for prediction of major pathologic response (MPR) in NSCLC-TRI recipients, in connection with various aspects discussed herein. Clinical variables that were individually significant in the training set (histology) were incorporated into logistic regression models alone and with QuanTAV response score, and evaluated on the testing set.

ADDITIONAL EMBODIMENTS

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing models to determine a response to therapy and/or prognosis for a tumor based at least in part on morphology and/or function features of tumor-associated vasculature that are not perceivable by the human eye, and involve computation that cannot be practically performed in the human mind. As one example, machine learning models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 21:
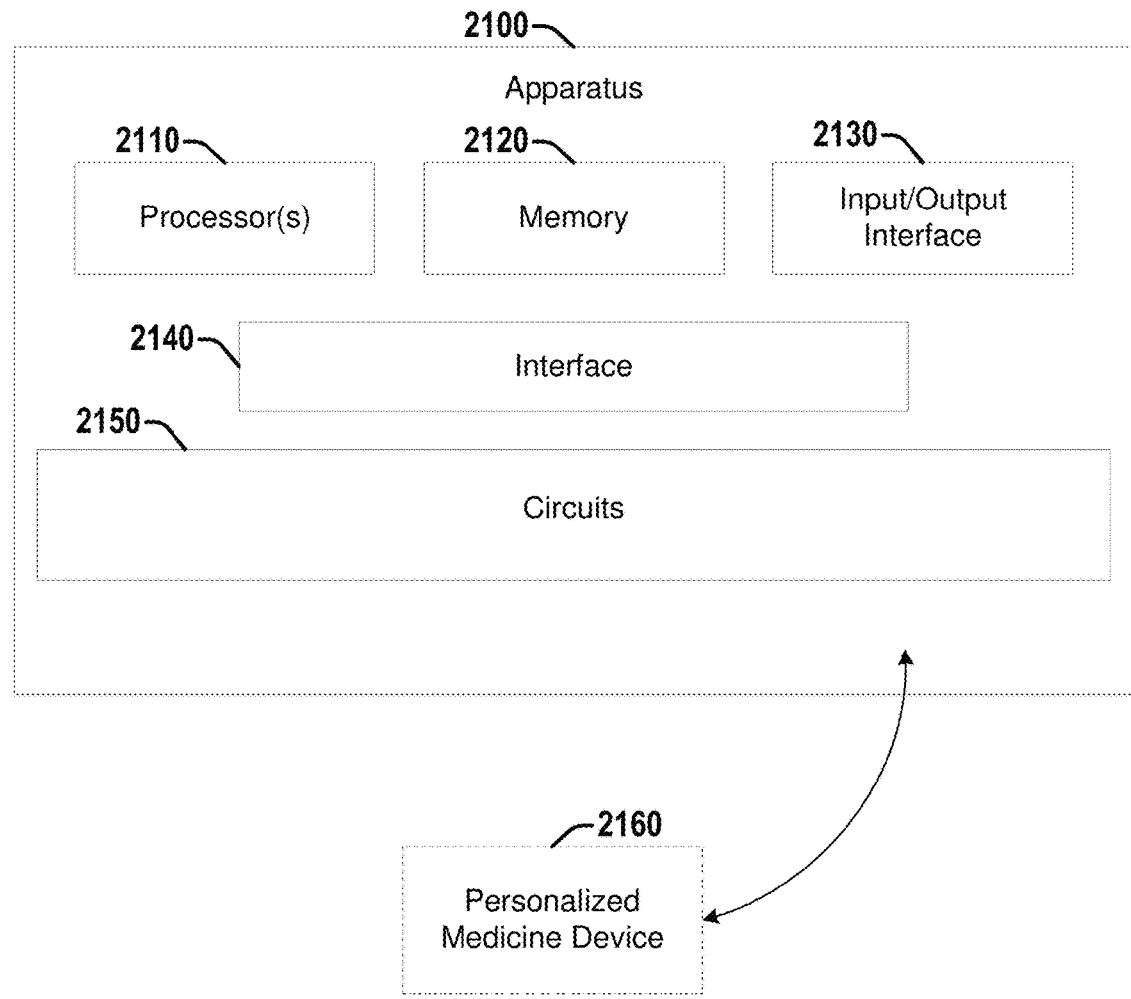
FIG. 21 illustrates a diagram of an example apparatus that can facilitate determination of a response to therapy or a prognosis for a tumor based at least in part on vessel morphological, spatial orientation, and/or functional features and/or can construct a machine learning (ML) classifier to perform such a determination, according to various embodiments discussed herein.

Referring to FIG. 21, illustrated is a diagram of an example apparatus 2100 that can facilitate determination of a response to therapy or a prognosis for a tumor based at least in part on vessel morphological, spatial orientation, /or functional features and/or can construct a machine learning (ML) classifier to perform such a determination, according to various embodiments discussed herein. Apparatus 2100 can be configured to perform various techniques discussed herein, for example, various operations discussed in connection with sets of operations 100, 200, 300, and/or other methods described herein. Apparatus 2100 can comprise one or more processors 2110 and memory 2120. Processor(s) 2110 can, in various embodiments, comprise circuitry such as, but not limited to, one or more single-core or multi-core processors. Processor(s) 2110 can include any combination of general-purpose processors and dedicated processors (e.g., graphics processors, application processors, etc.). The processor(s) can be coupled with and/or can comprise memory (e.g., of memory 2120) or storage and can be configured to execute instructions stored in the memory 2120 or storage to enable various apparatus, applications, or operating systems to perform operations and/or methods discussed herein. Memory 2120 can be configured to store one or more medical image volumes (e.g., obtained via MRI, CT, etc.) of a tumor (e.g., for training and/or determining a therapy response and/or prognosis). Each of the image(s) can comprise a plurality of pixels or voxels, each pixel or voxel having an associated intensity. Memory 2120 can be further configured to store additional data involved in performing operations discussed herein, such as for determining a therapy response and/or prognosis of a tumor based on morphological and/or functional TAV features and/or training a model to determine such a therapy response and/or prognosis, as discussed in greater detail herein.

Apparatus 2100 can also comprise an input/output (I/O) interface 2130 (e.g., associated with one or more I/O devices), a set of circuits 2150, and an interface 2140 that connects the processor(s) 2110, the memory 2120, the I/O interface 2130, and the set of circuits 2150. I/O interface 2130 can be configured to transfer data between memory 2120, processor 2110, circuits 2150, and external devices, for example, medical imaging device(s) (e.g., CT, MRI, etc.), and/or one or more remote devices for receiving inputs and/or providing outputs to a clinician, patient, etc., such as optional personalized medicine device 2160.

The processor(s) 2110 and/or one or more circuits of the set of circuits 2150 can perform one or more acts associated with a method or set of operations discussed herein, such as set of operations 100, 200, 300, etc. In various embodiments, different acts (e.g., different operations of a set of operations) can be performed by the same or different processor(s) 2110 and/or one or more circuits of the set of circuits 2150.

Apparatus 2100 can optionally further comprise personalized medicine device 2160. Apparatus 2100 can be configured to provide the predicted therapy response, predicted prognosis, and/or other data to personalized medicine device 2160. Personalized medicine device 2160 may be, for example, a computer assisted diagnosis (CADx) system or other type of personalized medicine device that can be used to facilitate monitoring and/or treatment of an associated medical condition. In some embodiments, processor(s) 2110 and/or one or more circuits of the set of circuits 2150 can be further configured to control personalized medicine device 2160 to display the predicted therapy response and/or prognosis for the tumor or other data on a computer monitor, a smartphone display, a tablet display, or other displays.

Examples herein can include subject matter such as an apparatus, a CT system, a MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting therapy response and/or prognosis for the tumor, according to embodiments and examples described.

One embodiment includes a non-transitory computer-readable storage device storing computer-executable instructions that when executed control a processor to perform operations comprising: accessing a pre-neoadjuvant chemotherapy (NAC) baseline dynamic contrast enhanced (DCE) magnetic resonance imaging (MRI) image of a region of tissue demonstrating breast cancer (BCa), where the baseline DCE-MRI image is associated with a patient, where the baseline DCE-MRI image is acquired prior to the administration of a contrast agent to the patient, where the baseline DCE-MRI image comprises a plurality of pixels, a pixel having an intensity, where the region of tissue includes a tumor region; accessing a set of post-contrast DCE-MRI images of the region of tissue; segmenting the tumor region represented in the baseline DCE-MRI image and the set of post-contrast DCE-MRI images; isolating tumor-associated vasculature represented in the baseline DCE-MRI image and the set of post-contrast DCE-MRI images; extracting a set of shape-based vasculature features from the tumor-associated vasculature represented in the baseline DCE-MRI image and the set of post-contrast DCE-MRI images; extracting a set of functional semi-quantitative pharmacokinetic (PK) measurements of temporal contrast enhancement changes from the set of post-contrast DCE-MRI images; providing the set of shape-based vasculature features and the set of functional semi-quantitative PK measurements to a machine learning classifier configured to generate a prediction of response to NAC based on the set of shape-based vascular features and the set of functional semi-quantitative PK measurements; receiving the prediction from the machine learning classifier; and generating a classification of the patient as a responder to NAC or non-responder based on the prediction.

In one embodiment, the set of shape-based vasculature features includes a curvature feature, a torsion feature, or a local orientation feature. In this embodiment, the set of functional semi-quantitative pharmacokinetic (PK) measurements includes a signal enhancement ratio, a time to peak enhancement, a rate of uptake, or a rate of washout.

In one embodiment, the machine learning classifier is a random forest classifier. In another embodiment, the machine learning classifier may be another, different type of machine learning classifier, or may be a deep learning model. Embodiments may further include training the machine learning classifier. Embodiments may further include testing the machine learning classifier.

Embodiments may further include displaying the classification, the prediction, the set of shape-based vasculature features, the set of functional semi-quantitative PK measurements, the set of post-contrast DCE-MRI images, or the baseline DCE-MRI image. Displaying the classification, the prediction, the set of shape-based vasculature features, the set of functional semi-quantitative PK measurements, the set of post-contrast DCE-MRI images, or the baseline DCE-MRI image on a computer monitor, a smartphone display, a tablet display, or other displays.

Operations, methods, and other embodiments described herein include acquiring electronic data, reading from a computer file, receiving a computer file, reading from a computer memory, or other computerized activity not practically performed in a human mind. For example, accessing the baseline dynamic DCE-MRI image, accessing the set of post-contrast DCE-MRI images, segmenting the tumor region, isolating tumor-associated vasculature represented in the baseline DCE-MRI image and the set of post-contrast DCE-MRI images, extracting the set of shape-based vasculature features or the set of functional semi-quantitative PK measurements, providing the set of shape-based vasculature features and the set of functional semi-quantitative PK measurements to the machine learning classifier, receiving the prediction from the machine learning classifier, and generating the classification include acquiring electronic data, reading from a computer file, receiving a computer file, reading from a computer memory, or other computerized activity not practically performed in a human mind.

Example 1 is a non-transitory computer-readable medium storing computer-executable instructions that, when executed, cause a processor to perform operations, comprising: accessing one or more medical imaging scans of a tumor, wherein the tumor is segmented on the one or more medical imaging scans; segmenting tumor-associated vasculature (TAV) associated with the tumor based on the one or more medical imaging scans; extracting one or more features from the TAV; providing the one or more features extracted from the TAV to a trained machine learning model; and receiving, from the machine learning model, one of a predicted response to a treatment for the tumor or a prognosis for the tumor.

Example 2 comprises the subject matter of any variation of any of example(s) 1, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 3 comprises the subject matter of any variation of any of example(s) 1-2, wherein the at least one feature comprises one or more of at least one TAV morphology feature, a statistic of the at least one TAV morphology feature, at least one TAV spatial organization feature, or the statistic of the at least one TAV spatial organization feature.

Example 4 comprises the subject matter of any variation of any of example(s) 3, wherein the statistic is one of a mean, a median, a standard deviation, a skewness, a kurtosis, a range, a minimum, a maximum, a percentile, or histogram frequencies.

Example 5 comprises the subject matter of any variation of any of example(s) 3-4, wherein the at least one feature comprises one or more of the at least one TAV morphology feature or the statistic of the at least one TAV morphology feature, wherein the at least one TAV morphology feature comprises one or more of a torsion per branch of a plurality of branches of the TAV, a curvature standard deviation per branch of the plurality of branches, a mean curvature per branch, a maximum curvature per branch per branch of the plurality of branches, a curvature skewness per branch of the plurality of branches, a curvature kurtosis per branch of the plurality of branches, a global vascular curvature, the torsion across the plurality of branches, a vessel volume, a vessel volume normalized to a volume of a region of interest comprising the tumor, a vessel volume normalized to a volume of the tumor, a total vessel length, a number of branches of the plurality of branches that enter the tumor, or a percentage of branches of the plurality of branches that enter the tumor.

Example 6 comprises the subject matter of any variation of any of example(s) 3-5, wherein the at least one feature comprises one or more of the at least one TAV spatial orientation feature or the statistic of the at least one TAV spatial orientation feature, wherein the at least one TAV spatial orientation feature comprises one or more of a vessel orientation along a XY projection image, a vessel orientation along a XZ projection image, a vessel orientation along a YZ projection image, a vessel orientation along a rotation-elevation projection image, a vessel orientation along a distance-rotation projection image, or a vessel orientation along a distance-elevation projection image.

Example 7 comprises the subject matter of any variation of any of example(s) 1-6, wherein the one or more features comprise at least one TAV function feature that measures a dynamics of a contrast agent in one or more of the tumor or the TAV, wherein the at least one TAV function feature is one or more of a signal enhancement ratio, a time to peak enhancement, a rate of uptake, or a rate of washout.

Example 8 comprises the subject matter of any variation of any of example(s) 1-7, wherein the one or more medical imaging scans comprise at least one of one or more computed tomography (CT) scans, one or more magnetic resonance imaging (MRI) scans without an addition of a contrast agent, or one or more MRI scans with the addition of the contrast agent.

Example 9 comprises the subject matter of any variation of any of example(s) 1-8, wherein the tumor is one a breast cancer tumor or a non-small cell lung cancer (NSCLC) tumor.

Example 10 comprises the subject matter of any variation of any of example(s) 1-9, wherein the predicted response to the treatment comprises a response score indicating a likelihood of pathologic complete response (pCR), major pathological response (MPR), or Response Evaluation Criteria In Solid Tumors (RECIST).

Example 11 comprises the subject matter of any variation of any of example(s) 1-10, wherein the prognosis for the tumor comprises one or more of a prognostic risk score or a risk group that indicates a likelihood of one or more of recurrence free survival (RFS) or progression free survival (PFS).

Example 12 is a non-transitory computer-readable medium storing computer-executable instructions that, when executed, cause a processor to perform operations, comprising: accessing a training set comprising a plurality of medical imaging scans, wherein each medical imaging scan of the training set comprises an associated tumor segmented on that medical imaging scan, wherein the associated tumor of that medical imaging scan is associated with at least one of a known response to a treatment or a known prognosis; and for each medical imaging scan of the training set: segmenting associated tumor-associated vasculature (TAV) for the associated tumor of that medical imaging scan; extracting associated values for a set of features from the associated TAV for the associated tumor of that medical imaging scan; and training a machine learning model based on the associated values extracted from the associated TAV for the associated tumor of that medical imaging scan and on the at least one of the known response to the treatment or the known prognosis.

Example 13 comprises the subject matter of any variation of any of example(s) 12, wherein the operations comprise: for each medical imaging scan of the training set, extracting associated values for a plurality of features from the associated TAV for the associated tumor of that medical imaging scan; and selecting the set of features from the plurality of features, wherein the set of features are identified as the best features for predicting the known response or the known prognosis.

Example 14 comprises the subject matter of any variation of any of example(s) 12-13, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 15 comprises the subject matter of any variation of any of example(s) 12-14, wherein the set of features comprises one or more of at least one TAV morphology feature, a statistic of the at least one TAV morphology feature, at least one TAV spatial organization feature, or the statistic of the at least one TAV spatial organization feature.

Example 16 comprises the subject matter of any variation of any of example(s) 15, wherein the statistic is one of a mean, a median, a standard deviation, a skewness, a kurtosis, a range, a minimum, a maximum, a percentile, or histogram frequencies.

Example 17 comprises the subject matter of any variation of any of example(s) 15-16, wherein the set of features comprises one or more of the at least one TAV morphology feature or the statistic of the at least one TAV morphology feature, wherein the at least one TAV morphology feature comprises one or more of a torsion per branch of a plurality of branches of the TAV, a curvature standard deviation per branch of the plurality of branches, a mean curvature per branch, a maximum curvature per branch per branch of the plurality of branches, a curvature skewness per branch of the plurality of branches, a curvature kurtosis per branch of the plurality of branches, a global vascular curvature, the torsion across the plurality of branches, a vessel volume, a vessel volume normalized to a volume of a region of interest comprising the tumor, a vessel volume normalized to a volume of the tumor, a total vessel length, a number of branches of the plurality of branches that enter the tumor, or a percentage of branches of the plurality of branches that enter the tumor.

Example 18 comprises the subject matter of any variation of any of example(s) 15-17, wherein the set of features comprises one or more of the at least one TAV spatial orientation feature or the statistic of the at least one TAV spatial orientation feature, wherein the at least one TAV spatial orientation feature comprises one or more of a vessel orientation along a XY projection image, a vessel orientation along a XZ projection image, a vessel orientation along a YZ projection image, a vessel orientation along a rotation-elevation projection image, a vessel orientation along a distance-rotation projection image, or a vessel orientation along a distance-elevation projection image.

Example 19 comprises the subject matter of any variation of any of example(s) 12-18, wherein the one or more features comprise at least one TAV function feature that measures a dynamics of a contrast agent in one or more of the tumor or the TAV, wherein the at least one TAV function feature is one or more of a signal enhancement ratio, a time to peak enhancement, a rate of uptake, or a rate of washout.

Example 20 comprises the subject matter of any variation of any of example(s) 12-19, wherein the medical imaging scan comprises a computed tomography (CT) scan, a magnetic resonance imaging (MRI) scan without an addition of a contrast agent, or an MRI scan with the addition of the contrast agent.

Example 21 comprises the subject matter of any variation of any of example(s) 12-20, wherein the tumor is one a breast cancer tumor or a non-small cell lung cancer (NSCLC) tumor.

Example 22 is an apparatus, comprising: memory configured to store a medical imaging scan of a tumor, wherein the tumor is segmented on the medical imaging scan; one or more processors configured to: segment tumor-associated vasculature (TAV) associated with the tumor based on the medical imaging scan; extract one or more features from the TAV; provide the one or more features extracted from the TAV to a trained machine learning model; and receive, from the machine learning model, one of a predicted response to a treatment for the tumor or a prognosis for the tumor.

Example 23 comprises the subject matter of any variation of any of example(s) 22, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

Example 24 comprises the subject matter of any variation of any of example(s) 22-23, wherein the at least one feature comprises one or more of at least one TAV morphology feature, a statistic of the at least one TAV morphology feature, at least one TAV spatial organization feature, or the statistic of the at least one TAV spatial organization feature.

Example 25 comprises the subject matter of any variation of any of example(s) 24, wherein the statistic is one of a mean, a median, a standard deviation, a skewness, a kurtosis, a range, a minimum, a maximum, a percentile, or histogram frequencies.

Example 26 comprises the subject matter of any variation of any of example(s) 24-25, wherein the at least one feature comprises one or more of the at least one TAV morphology feature or the statistic of the at least one TAV morphology feature, wherein the at least one TAV morphology feature comprises one or more of a torsion per branch of a plurality of branches of the TAV, a curvature standard deviation per branch of the plurality of branches, a mean curvature per branch, a maximum curvature per branch per branch of the plurality of branches, a curvature skewness per branch of the plurality of branches, a curvature kurtosis per branch of the plurality of branches, a global vascular curvature, the torsion across the plurality of branches, a vessel volume, a vessel volume normalized to a volume of a region of interest comprising the tumor, a vessel volume normalized to a volume of the tumor, a total vessel length, a number of branches of the plurality of branches that enter the tumor, or a percentage of branches of the plurality of branches that enter the tumor.

Example 27 comprises the subject matter of any variation of any of example(s) 24-26, wherein the at least one feature comprises one or more of the at least one TAV spatial orientation feature or the statistic of the at least one TAV spatial orientation feature, wherein the at least one TAV spatial orientation feature comprises one or more of a vessel orientation along a XY projection image, a vessel orientation along a XZ projection image, a vessel orientation along a YZ projection image, a vessel orientation along a rotation-elevation projection image, a vessel orientation along a distance-rotation projection image, or a vessel orientation along a distance-elevation projection image.

Example 28 comprises the subject matter of any variation of any of example(s) 22-27, wherein the one or more features comprise at least one TAV function feature that measures a dynamics of a contrast agent in one or more of the tumor or the TAV, wherein the at least one TAV function feature is one or more of a signal enhancement ratio, a time to peak enhancement, a rate of uptake, or a rate of washout.

Example 29 comprises the subject matter of any variation of any of example(s) 22-27, wherein the predicted response to the treatment comprises a response score indicating a likelihood of pathologic complete response (pCR), major pathological response (MPR), or Response Evaluation Criteria In Solid Tumors (RECIST).

Example 30 comprises the subject matter of any variation of any of example(s) 22, wherein the prognosis for the tumor comprises one or more of a prognostic risk score or a risk group that indicates a likelihood of one or more of recurrence free survival (RFS) or progression free survival (PFS).

Example 31 comprises an apparatus comprising means for executing any of the described operations of examples 1-30.

Example 32 comprises a machine readable medium that stores instructions for execution by a processor to perform any of the described operations of examples 1-30.

Example 33 comprises an apparatus comprising: a memory; and one or more processors configured to: perform any of the described operations of examples 1-30.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method, comprising:
    accessing data derived from one or more routine clinical medical imaging scans including a lesion in which the lesion and associated vasculature are segmented in a three-dimensional segmentation;
    extracting at least two features, the at least two features including at least one feature indicative of a morphology of the associated vasculature or a portion thereof, and at least one feature indicative of a function of the associated vasculature or a portion thereof, the at least one feature indicative of the morphology extracted from the three-dimensional segmentation of the associated vasculature, and the at least one feature indicative of the function being a pharmacokinetic measurement extracted from a region of tissue in the one or more routine clinical imaging scans that is perfused by the associated vasculature;
    providing the at least two features, and/or one or more statistics of the at least two features, to a machine learning model trained to make a prediction concerning the lesion; and
    receiving, from the machine learning model, the prediction concerning the lesion.

2. The method of claim 1, wherein the prediction concerning the lesion comprises one of a predicted response to a treatment for the lesion or a prognosis for the lesion.

3. The method of claim 2, wherein the prediction concerning the lesion concerns response to neoadjuvant chemotherapy for the lesion.

4. The method of claim 1, wherein the at least one feature indicative of the morphology of the associated vasculature comprises one or more of a torsion per branch of a plurality of branches of the associated vasculature, a curvature standard deviation per branch of the plurality of branches, a mean curvature per branch, a maximum curvature per branch of the plurality of branches, a curvature skewness per branch of the plurality of branches, a curvature kurtosis per branch of the plurality of branches, a global vascular curvature, the torsion across the plurality of branches, a vessel volume, a vessel volume normalized to a volume of a region of interest comprising the lesion, a vessel volume normalized to a volume of the lesion, a total vessel length, a number of branches of the plurality of branches that enter the lesion, or a percentage of branches of the plurality of branches that enter the lesion.

5. The method of claim 1, wherein the pharmacokinetic measurement comprises a measurement comprises a measurement of temporal contrast enhancement changes.

6. The method of claim 5, wherein the pharmacokinetic measurement of temporal contrast enhancement changes comprises signal enhancement ratio, time to peak enhancement, rate of uptake, or rate of washout.

7. The method of claim 1, wherein the machine learning model is one of, or an ensemble of two or more of, a logistic regression model, a Cox regression model, a Least Absolute Shrinkage and Selection Operator (LASSO) regression model, a naïve Bayes classifier, a support vector machine (SVM) with a linear kernel, a SVM with a radial basis function (RBF) kernel, a linear discriminant analysis (LDA) classifier, a quadratic discriminant analysis (QDA) classifier, a logistic regression classifier, a decision tree, a random forest, a diagonal LDA, a diagonal QDA, a neural network, an AdaBoost algorithm, an elastic net, a Gaussian process classification, or a nearest neighbors classification.

8. A non-transitory computer-readable medium storing computer-executable instructions that, when executed, cause a processor to perform the method of claim 1.

9. An apparatus, comprising:
    memory configured to store data derived from one or more routine clinical medical imaging scans including a lesion, wherein the lesion and associated vasculature are segmented in a three-dimensional segmentation; and
    one or more processors configured to:
        access the data derived from one or more routine clinical medical imaging scans including the lesion in which the lesion and the associated vasculature are segmented in the three-dimensional segmentation,
        extract at least two features, the at least two features including at least one feature indicative of a morphology of the associated vasculature or a portion thereof, and at least one feature indicative of a function of the associated vasculature or a portion thereof, the at least one feature indicative of the morphology extracted from the three-dimensional segmentation of the associated vasculature, and the at least one feature indicative of the function being a pharmacokinetic measurement extracted from a region of tissue in the one or more routine clinical imaging scans that is perfused by the associated vasculature, and provide the at least two features, and/or one or more statistics of the at least two features, to a machine learning model trained to make a prediction concerning the lesion.

10. The apparatus of claim 9, wherein the at least one feature indicative of the morphology includes a feature describing a vessel orientation.

11. The apparatus of claim 9, wherein the at least one feature indicative of the function includes a pharmacokinetic measurement of temporal contrast enhancement changes.

12. The apparatus of claim 9, wherein the prediction relates to a response to neoadjuvant chemotherapy.

13. A method, comprising:
accessing data derived from one or more routine clinical medical imaging scans including a lesion in which the lesion and associated vasculature are segmented in a three-dimensional segmentation;
extracting at least one feature indicative of a spatial organization of the associated vasculature, the at least one feature taken from a projection onto a plane of at least a portion of the three-dimensional segmentation of the associated vasculature;
providing the at least one feature and/or at least one statistic of the at least one feature to a trained machine learning model; and
receiving, from the trained machine learning model, a prediction concerning the lesion.

14. The method of claim 13, wherein the prediction concerning the lesion comprises one of a predicted response to a treatment for the lesion or a prognosis for the lesion.

15. The method of claim 14, wherein the prediction concerns response to neoadjuvant chemotherapy for the lesion.

16. The method of claim 13, wherein the at least one feature indicative of the spatial organization of the associated vasculature comprise one or more of a vessel orientation along a XY projection image, a vessel orientation along a XZ projection image, a vessel orientation along a YZ projection image, a vessel orientation along a rotation-elevation projection image, a vessel orientation along a distance-rotation projection image, or a vessel orientation along a distance-elevation projection image.

17. The method of claim 13, further comprising:
extracting at least one feature indicative of a morphology of the associated vasculature; and
providing the at least one feature indicative of the spatial organization and the at least one feature indicative of a morphology and/or statistics thereof to the trained machine learning model.

18. The method of claim 17, further comprising:
identifying branches of the associated vasculature in the three-dimensional segmentation;
wherein the at least one feature indicative of morphology is based, at least in part, on the branches of the associated vasculature.

19. The method of claim 17, wherein the at least one feature indicative of the morphology comprises one or more of a torsion per branch of a plurality of branches of the associated vasculature, a curvature standard deviation per branch of the plurality of branches, a mean curvature per branch, a maximum curvature per branch of the plurality of branches, a curvature skewness per branch of the plurality of branches, a curvature kurtosis per branch of the plurality of branches, a global vascular curvature, the torsion across the plurality of branches, a vessel volume, a vessel volume normalized to a volume of a region of interest comprising the lesion, a vessel volume normalized to a volume of the lesion, a total vessel length, a number of branches of the plurality of branches that enter the lesion, or a percentage of branches of the plurality of branches that enter the lesion.

20. A non-transitory computer-readable medium storing computer-executable instructions that, when executed, cause a processor to perform the method of claim 13.

* * * * *